(12) United States Patent
Hoberman et al.

(10) Patent No.: US 7,437,190 B1
(45) Date of Patent: Oct. 14, 2008

(54) CARDIAC STIMULATION DEVICE WITH ADJUSTABLE BLANKING INTERVALS

(75) Inventors: Katie Hoberman, South Pasadena, CA (US); Peter Boileau, Valencia, CA (US)

(73) Assignee: Pacesetter, Inc., Sylmar, CA (US)

( * ) Notice: Subject to any disclaimer, the term of this patent is extended or adjusted under 35 U.S.C. 154(b) by 708 days.

(21) Appl. No.: 10/792,082

(22) Filed: Mar. 2, 2004

(51) Int. Cl.
A61N 1/362 (2006.01)
(52) U.S. Cl. .......................................................... 607/9
(58) Field of Classification Search ................. 607/4–9, 607/14, 27–28, 30–32; 600/510
See application file for complete search history.

(56) References Cited

U.S. PATENT DOCUMENTS

| | | | |
|---|---|---|---|
| 4,515,161 A | 5/1985 | Wittkampf et al. | |
| 5,584,867 A | 12/1996 | Limousin et al. | |
| 5,591,214 A | 1/1997 | Lu | |
| 5,658,320 A | 8/1997 | Betzold et al. | 607/14 |
| 5,735,881 A | 4/1998 | Routh et al. | |
| 6,122,545 A | 9/2000 | Struble et al. | |
| 6,438,421 B1 | 8/2002 | Stahmann et al. | 607/9 |
| 6,477,416 B1 | 11/2002 | Florio et al. | 607/9 |
| 6,501,988 B2 | 12/2002 | Kramer et al. | 607/9 |
| 6,512,952 B2 | 1/2003 | Stahmann et al. | 607/9 |
| 6,611,714 B1 | 8/2003 | Mo | |
| 6,625,490 B1 | 9/2003 | McClure et al. | 607/9 |
| 6,643,547 B2 * | 11/2003 | Kim | 607/14 |
| 6,687,539 B2 | 2/2004 | Gilkerson et al. | 607/5 |
| 6,731,980 B1 | 5/2004 | Mouchawar et al. | 607/9 |
| 6,871,097 B1 | 3/2005 | Strandberg | |
| 6,873,875 B1 | 3/2005 | Gilkerson et al. | |
| 6,934,585 B1 * | 8/2005 | Schloss et al. | 607/9 |
| 2002/0082650 A1 | 6/2002 | Stahmann et al. | |
| 2002/0082653 A1 | 6/2002 | Stahmann et al. | |
| 2002/0193835 A1 | 12/2002 | Baker | |
| 2004/0010295 A1 | 1/2004 | Kramer et al. | 607/25 |
| 2004/0049235 A1 | 3/2004 | Deno et al. | 607/9 |
| 2004/0210264 A1 | 10/2004 | Kleckner et al. | 607/25 |
| 2005/0125041 A1 | 6/2005 | Min et al. | 607/9 |

FOREIGN PATENT DOCUMENTS

| | | |
|---|---|---|
| EP | 1 038 548 A2 | 9/2000 |
| EP | 1 038 548 A3 | 3/2001 |

(Continued)

OTHER PUBLICATIONS

Schreieck, Jurgen et al., "*Inappropriate Shock Delivery Due to Ventricular Double Detection with a Biventricular Pacing Implantable Cardioverter Defibrillator,*" PACE, vol. 24, No. 7 (Jul. 2001), pp. 1154-1157.

(Continued)

Primary Examiner—Mark Bockelman

(57) ABSTRACT

An implantable cardiac stimulating device employs different post-ventricular atrial refractory periods for different types of ventricular events, such as a sensed ventricular event and a paced ventricular event. A controller facilitates selection or adjustment by remote programming of two different post-ventricular atrial blanking intervals that are invoked depending upon the type of ventricular event. A set of discrete blanking interval values may be available for programming the different blanking intervals, and a search routine may be executed to systematically apply the different blanking interval values and determine a suitable value by determining whether far-field R-waves are detected after expiration of each applied blanking interval value.

26 Claims, 8 Drawing Sheets

FOREIGN PATENT DOCUMENTS

WO          WO 97/11748          4/1997

OTHER PUBLICATIONS

Queiroga, Andrea et al. "*Overdrive Pacing for Atrial Fibrillation—Complications and Ways to Overcome Them*," Europace Supplements, vol. 2 (Jun. 2001), p. B203—ABSTRACT.

Kawanishi, David et al., "*Closer Investigation of Oversensing: Sense Amplifier Signal Analysis*," Europace Supplements, vol. 2 (Jun. 2001), p. B146—ABSTRACT.

Restriction Requirement, mailed Jul. 11, 2005: Related U.S. Appl. No. 10/794,566.

NonOffice Action, mailed Aug. 25, 2005: Related U.S. Appl. No. 10/794,566.

NonFinal Office Action, mailed Dec. 2, 2005: Related U.S. Appl. No. 10/794,566.

NonFinal Office Action, mailed May 11, 2006: Related U.S. Appl. No. 10/794,566.

NonFinal Office Action, mailed Oct. 13, 2006: Related U.S. Appl. No. 10/794,566.

Final Office Action, mailed Mar. 26, 2007: Related U.S. Appl. No. 10/794,566.

NonOffice Action, mailed Jul. 15, 2005: Related U.S. Appl. No. 10/794,565.

NonFinal Office Action, mailed Nov. 8, 2005: Related U.S. Appl. No. 10/794,565.

Advisory Action, mailed Feb. 14, 2006: Related U.S. Appl. No. 10/794,565.

NonFinal Office Action, mailed Mar. 31, 2006: Related U.S. Appl. No. 10/794,565.

Final Office Action, mailed Sep. 13, 2006: Related U.S. Appl. No. 10/794,565.

Advisory Action, mailed Nov. 8, 2006: Related U.S. Appl. No. 10/794,565.

NonFinal Office Action, mailed Apr. 16, 2007: Related U.S. Appl. No. 10/794,565.

NonFinal Office Action, mailed Aug. 27, 2007: Related U.S. Appl. No. 10/794,565.

Notice of Allowance, mailed Dec. 12, 2007: Related Application Ser. No. 10/794,565.

Notice of Allowance, mailed Mar. 31, 2008: Related Application Ser. No. 10/794,565.

\* cited by examiner

CARDIAC STIMULATION DEVICE WITH ADJUSTABLE BLANKING INTERVALS

FIELD OF THE INVENTION

The field of the present invention generally relates to methods and apparatus for cardiac stimulation and, more particularly, to implantable cardiac stimulation devices for monitoring and pacing the heart.

BACKGROUND

Cardiac stimulation devices (such as implantable pacemakers and implantable cardioverter-defibrillators ("ICDs")) are generally capable of rectifying a patient's abnormal heart rhythm by delivering appropriately timed stimulation signals to one or more chambers of the heart, thereby causing the heart to contract in a synchronous pattern and better perform its primary function of blood circulation.

Cardiac stimulation devices that monitor or pace both the atrium and ventricle of the heart generally need to distinguish between atrial and ventricular events in order to employ the proper therapy with the appropriate timing. However, it is possible for ventricular events to be detected on an atrial detection channel, thus causing the implanted device to mistakenly interpret the detected signal as an atrial event and potentially deliver an erroneous pacing therapy in response. Ventricular events detected by the atrial channel are commonly referred to as "far-field R-waves" and usually are observable by the atrial channel shortly after the ventricular activity (due to propagation delay of the R-wave to the atria of the heart). A common technique for avoiding detection of far-field R-waves is to "blank" the atrial channel for a prescribed period of time during which far-field R-waves are expected to occur. The timing interval following an atrial event is generally known as a post-ventricular atrial blanking (PVAB) interval. The post-ventricular atrial blanking interval generally begins with the ventricular paced or sensed event, and all atrial events occurring the interval are, generally, neither detected nor counted in the various rate calculations. Once the post-ventricular atrial blanking interval has expired, the atrial channel can, if desired, be used to detect cardiac activity.

While the use of a post-ventricular atrial blanking interval is beneficial, a single predefined blanking interval may not be suitable for all patients and all circumstances. Also, it may not be convenient to identify the most suitable blanking interval for a given patient. It would therefore be advantageous, for example, to provide increased flexibility in a cardiac stimulation device with respect to blanking intervals, and further to provide convenient tools to physicians to assist determination of a blanking interval suitable for a particular patient.

SUMMARY

What is described herein, in one embodiment, is generally directed to an implantable cardiac stimulation device having different post-ventricular atrial refractory periods for different types of ventricular activity, and associated methods.

In one aspect, an implantable cardiac stimulation device comprises a pulse generator for generating stimulating pulses to be applied to a patient's heart, a detector for detecting activity in the patient's heart, and a controller configured to apply or select a post-ventricular atrial blanking interval based upon the type of cardiac event or activity.

In other aspects and embodiments, at least two post-ventricular atrial blanking interval values are provided, including a first post-ventricular atrial blanking interval employed after ventricular pace events, and a second post-ventricular atrial blanking interval employed after ventricular sense events. Furthermore, the controller, which may functionally be part of the implantable device or external thereto, may be configured to allow selection of the programmable post-ventricular atrial blanking period interval values from among a plurality of discrete atrial blanking period interval values, and/or to execute an automated routine to search for and select the post-ventricular atrial blanking intervals. The search routine may, for example, systematically apply the discrete atrial blanking period interval values and monitor whether far-field R-waves are detected by the detector after expiration of each applied discrete atrial blanking period interval value.

In another aspect, a method is provided comprising the steps of detecting activity in the atrium and ventricle of a patient's heart; applying a first post-ventricular atrial blanking period interval after a sensed ventricular event; applying a second post-ventricular atrial blanking period interval after a paced ventricular event; and selecting a value for at least one of the first and second post-ventricular atrial blanking period intervals from among a plurality of discrete atrial blanking period interval values.

In other aspects and embodiments, the foregoing method may involve selecting values for one or both of the first and second post-ventricular atrial blanking period intervals from among the plurality of discrete atrial blanking period interval values (which may differ for the first and second post-ventricular atrial blanking period intervals). In addition, the method may involve execution of a search routine to determine the atrial blanking period interval values.

Further embodiments, variations and enhancements are also disclosed herein.

BRIEF DESCRIPTION OF THE DRAWINGS

FIG. 5 is a graph illustrating the effect of a post-ventricular atrial blanking interval that is too long for a particular patient or condition, while

DETAILED DESCRIPTION OF THE PREFERRED EMBODIMENT

In one aspect, an implantable cardiac stimulation device employs different post-ventricular atrial blanking intervals, one or more of which may be programmable, for different types of ventricular activity. In addition, a search routine may be used for facilitating determination of the post-ventricular atrial blanking interval(s). As previously described herein, a single predefined blanking interval may not be suitable for all patients and all circumstances. If, for example, a post-ventricular atrial blanking (PVAB) interval is too long for a particular patient, the implanted device may lose the ability to sense high rate atrial events and possibly delay delivering appropriate therapy such as, e.g., mode switching.

Figure 5:
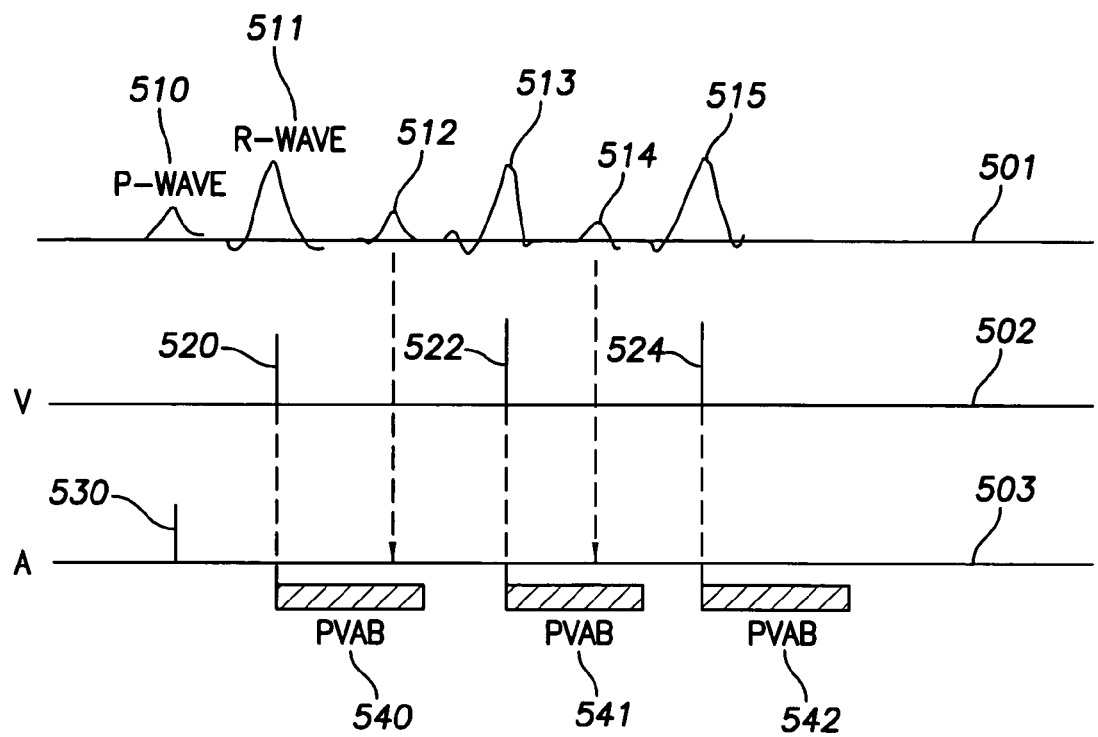

This situation is illustrated, for example, in FIG. 5. As shown in this example, on graph 501, P-waves 510, 512, 514 indicative of atrial activity are occurring at a relatively high rate. Each P-wave 510, 512, and 514 is followed by a corresponding R-wave 511, 513, and 515, respectively, indicative of ventricular activity. A post-ventricular atrial blanking ("PVAB") interval 540, 541, and 542 is timed out by the cardiac stimulation device following each ventricular event 511, 513, and 515. Graph 502 illustrates detection by the cardiac stimulation device of ventricular activity, while graph 503 illustrates detection by the device of atrial activity. The first P-wave 510 is detected by the device and registers an atrial event 530 as shown on graph 503. The immediately following R-wave 511 is likewise detected by the device and registers a ventricular event 520 as shown on graph 502. Following the ventricular event 520, the device times out the PVAB interval 540. During the PVAB 540, the atrial detection circuitry is rendered inactive and will not detect atrial activity. However, because the PVAB interval 540 is programmed with a value that is too long from a physiological standpoint, the next P-wave 512, which occurs relatively rapidly after the R-wave 512 because of the high intrinsic heart rate, is not detected by the atrial detection circuitry since the P-wave 512 occurs during the PVAB interval 540 during which the atrial detection circuitry is inactive. Nevertheless, the immediately following R-wave 513 is detected and registers as a ventricular event 522 on the ventricular channel. Another PVAB interval 541 is timed out, but again the following P-wave 514 is missed due to the inappropriate length of the PVAB interval 541. The following R-wave 515 is detected on the ventricular channel, registering as ventricular event 524. This cycle continues, with the device's atrial detection ability lost or compromised due to the length of the PVAB interval.

In some cases, due the lack of a detected intervening P-wave, the device may erroneously treat the R-waves 513 and/or 515 as premature ventricular contractions (PVC), which in turn may lead to the delivery of inappropriate therapy by the device. Moreover, the device may possibly delay the delivery of appropriate therapy, such as mode-switching, based on high detected atrial rates.

Figure 6:
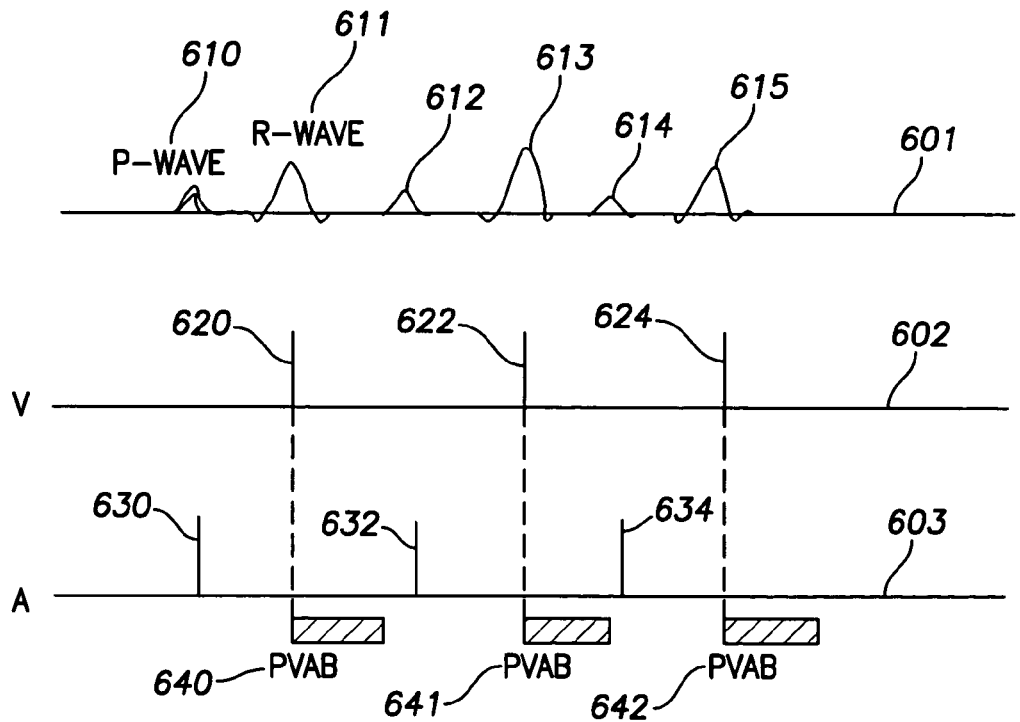
FIG. 6 illustrates the effect of programming a shorter blanking interval.

FIG. 6 illustrates a situation in which the post-ventricular atrial blanking interval has been shortened to alleviate the problems illustrated in FIG. 5. FIG. 6 shows the same pattern of P-waves 610, 612, and 614 and R-waves 611, 613, and 615 as in FIG. 5. However, due to the shortened PVAB intervals 640, 641, and 642, each of P-waves 610, 612, and 614 results in a detected atrial event 630, 632, and 634 on the atrial channel.

Nonetheless, while a shortened PVAB interval may alleviate detection problems when atrial activity is relatively high, problems may also occur if the post-ventricular atrial blanking interval is programmed too short. For example, in such a situation, inappropriate sensing of far-field R-waves or other evoked activity may occur, possibly leading to inappropriate mode switching or a delay in returning to an atrial-based timing mode.

In addition, it is known that different types of ventricular events lead to different far-field R-wave timing. For example, according to one particular study, it has been observed that sensed ventricular events lead to far-field R-waves which manifest roughly between 37 to 50 milliseconds after the sensed event, whereas paced ventricular events lead to far-field R-waves which manifest roughly between 115 to 129 milliseconds after the paced event. Thus, a single post-ventricular atrial blanking period used following both paced and sensed ventricular events may be less than optimal. If tailored for the "worst case"—i.e., following paced events—then the PVAB interval may in fact be considerably longer than necessary, particularly following sensed ventricular events.

It would therefore be beneficial to provide a cardiac stimulation device in which the PVAB interval can be tailored for a specific patient. Accordingly, a device which allows programmability of blanking intervals and convenient determination thereof may be advantageous. In one type of implantable cardiac pacing device disclosed herein, different PVAB periods may be invoked depending upon whether the triggering ventricular event was, for example, a paced event or a sensed event. In period following a sensed ventricular event and a longer PVAB period following a paced ventricular event.

Figure 1:
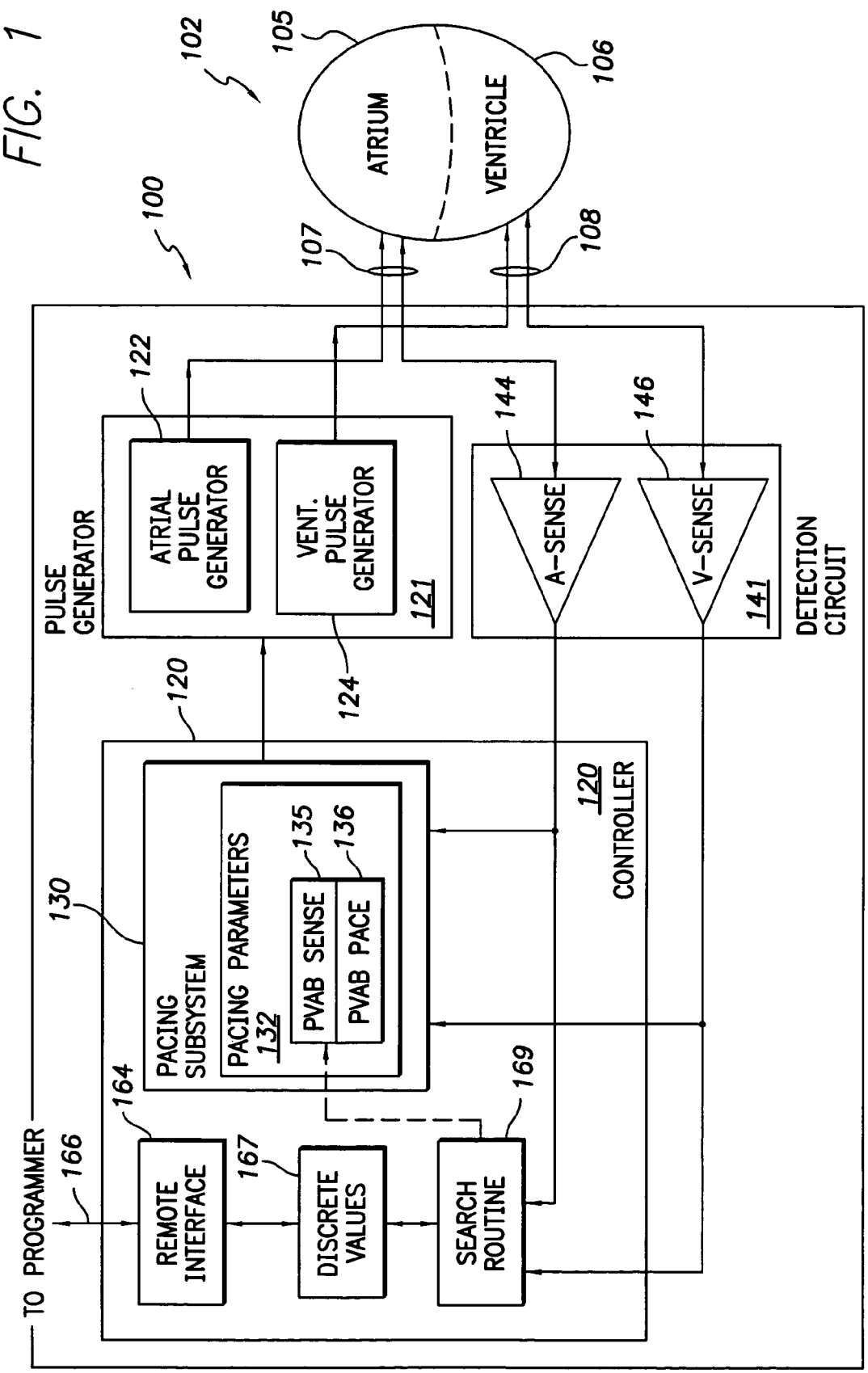
FIG. 1 is a simplified, functional block diagram depicting various features of a cardiac stimulation device in communication with a patient's heart according to one embodiment as disclosed herein.

FIG. 1 is a simplified block diagram illustrating an implantable cardiac stimulation device 100, as may be utilized in connection with one or more embodiments disclosed herein, in communication with a patient's heart 102. In the particular example illustrated in FIG. 1, the implantable cardiac stimulation device 100 is electrically connected to the patient's heart 102 by way of multiple leads 107 and 108, suitable for multi-chamber sensing and delivery of stimulating pulses (and, if employed in a device having cardioversion and/or defibrillation capabilities, shock therapy). Generally, the implantable cardiac stimulation device 100 senses cardiac activity in, and delivers stimulating pulses (and/or electrical shocks) to, the atria 105 and ventricles 106 of the patient's heart 102 via leads 107 and 108. While the cardiac stimulation device 100 of FIG. 1 is generally described in the context of a dual-chamber device with multiple therapy capabilities (e.g., pacing, cardioversion, and defibrillation functions), it will be understood that the description is equally applicable to other devices such as, e.g., a device that has biatrial and/or biventricular sensing and pacing capabilities, a device that lacks means for delivering cardioversion or defibrillation therapies, or to other simpler or more complex devices. Those skilled in the art will appreciate that various components or features in the implantable cardiac stimulation device 100 could be duplicated, eliminated, or disabled, in various combinations, while still operating according to the principles as described herein, and that various additional circuits, systems, subsystems, components, or features may be added without departing from the scope and spirit of the basic principles described herein. The depiction in FIG. 1 is thus meant to be illustrative of certain features that may be found in a cardiac stimulation device 100 but is not intended to limit the scope of the invention in any manner.

The cardiac stimulation device system 100 is preferably configured to be capable of providing pacing stimulation therapies in one or more chambers of the patient's heart for treating various heart conditions such as bradycardia. Additionally, the cardiac stimulation device 100 may be configured to provide cardioversion and/or defibrillation therapies to the patient's heart for treating, e.g., fast or slow arrhythmias or other heart conditions.

The implantable cardiac stimulation device 100 preferably senses cardiac activity and applies electrical stimulation therapies through leads 107, 108. To sense atrial cardiac signals and to provide right atrial chamber stimulation therapy, the implantable cardiac stimulation device 100 is preferably coupled to an implantable right atrial lead 107 having, for example, an atrial tip electrode which may be implanted in the patient's right atrial appendage. To sense left atrial and ventricular cardiac signals and to provide left chamber pacing therapy, implantable cardiac stimulation device 100 is preferably coupled to a coronary sinus lead 108 designed for placement in the coronary sinus region via the coronary sinus by positioning a distal electrode adjacent to the left ventricle and/or additional electrode(s) adjacent to the left atrium. The coronary sinus region in the present context generally refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus. A preferred coronary sinus lead is configured to receive atrial and ventricular cardiac signals, and to deliver left ventricular pacing therapy using a left ventricular tip electrode, left atrial pacing therapy using a left atrial ring electrode, and shocking therapy (if provided) using a left atrial coil electrode 126. In each case, the electrical return path may be a different lead or the housing of the implantable cardiac stimulation device 100 itself, according to the particular design employed.

The leads 108 coupled to the implantable cardiac stimulation device 100 may also include an implantable right ventricular lead having, for example, a right ventricular tip electrode, a right ventricular ring electrode/sensor, a right ventricular (RV) coil electrode, and a superior vena cava (SVC) coil electrode, as is well known in the art. In typical implantations, the right ventricular lead is transvenously inserted into the heart 102 in a manner such that the right ventricular tip electrode is positioned in the right ventricular apex, the RV coil electrode is positioned in the right ventricle, and the SVC coil electrode is positioned in the superior vena cava. The right ventricular lead is thereby capable of receiving cardiac signals, and delivering stimulation to the right ventricle in the form of pacing therapy and, if desired, shock therapy.

The implantable cardiac stimulation device 100 may be housed in a sealed encasement, which can be used if desired as an "electrode" connection for various unipolar pacing modes or shock therapies, and which is generally referred to as the "can," "case" or "case electrode."

Operation of the implantable cardiac stimulation device is preferably controlled by a programmable microcontroller 120. Microcontroller 120 may comprise components which are typical in implantable cardiac stimulation devices—for example, a microprocessor (or equivalent digital circuitry) adapted for controlling the delivery of stimulation therapy, volatile (e.g., RAM) and/or non-volatile (e.g., ROM) memory, logic and timing circuitry, state machine circuitry, and I/O circuitry. The microcontroller 120 preferably includes the ability to process or monitor input signals (data) as controlled by a program code stored in memory. The specific type of microcontroller 120 is not essential to the described implementations. Rather, any suitable microcontroller 120 may be used that is capable of carrying out the functions described herein. The use of microprocessor-based control circuits for performing timing and data analysis functions are well known in the art.

The implantable cardiac stimulation device 100 further may comprise an atrial pulse generator 122 and a ventricular pulse generator 124, collectively illustrated as pulse generator 121 in FIG. 1, for generating pacing stimulation pulses to be delivered to the heart 102 via the various leads 107, 108. To provide stimulation therapy in each of the four chambers of the heart, the atrial and ventricular pulse generators 122, 124 may include dedicated, independent pulse generators, multiplexed pulse generators, or shared pulse generators. In the example shown in FIG. 1, the pulse generators 122, 124 may be controlled by a pacing subsystem 130 (which may itself be a part of or under control of the microcontroller 120, but is shown as a separate functional block for purposes of illustration) through control signals which trigger or inhibit the stimulation pulses.

The pacing subsystem 130 and/or microcontroller 120 may include, in the form of, e.g., digital circuitry, microcode or program instructions, or a combination thereof, various functional components which facilitate control of the various aspects of the implantable cardiac stimulation device 100. For example, the pacing subsystem 130 and/or microcontroller 120 may include timing control circuitry to control the timing of the stimulation pulses (e.g., pacing rate, atrio-ventricular (AV) delay, atrial interconduction (A-A) delay, or ventricular interconduction (V-V) delay, etc.) as well as to keep track of the timing of refractory periods, blanking intervals, noise detection windows, evoked response windows, alert intervals, marker channel timing, etc. These types of timing functions are generally well known in the art.

To sense activity in any or all chambers of the heart, atrial sensing circuit 144 and ventricular sensing circuit 146 may be selectively coupled to the various leads 107, 108 through, e.g., an electronic configuration switch. The atrial sensing circuit 144 and ventricular sensing circuit 146 may include, for example, one or more low power, precision amplifiers with programmable gain and/or automatic gain control, band-pass filtering, and threshold detection circuitry, as known in the art, to selectively sense the cardiac signal of interest. The automatic gain control may assist in sensing low amplitude signal characteristics. The electronic configuration switch preferably determines the "sensing polarity" of the cardiac signal by selectively opening/closing the appropriate internal switches, in a manner well understood in the art. The foregoing features allow the physician to program the sensing polarity independent of the stimulation polarity.

The outputs of the atrial and ventricular sensing circuits 144 and 146 are connected to the pacing subsystem 130 which, in turn, is able to trigger or inhibit the atrial and ventricular pulse generators 122 and 124, respectively, in a programmable fashion in response to the absence or presence of cardiac activity in the appropriate chambers of the heart. The detection circuit 141 may, in turn, receive control signals from the microcontroller 120 or otherwise for purposes of controlling the gain or threshold of the sensing circuits 144, 146, any polarization charge removal circuitry (not shown), and/or the timing of any blanking circuitry (not shown) coupled to the inputs of the sensing circuits 144, 146, all in a manner well understood in the art.

For arrhythmia detection, the implantable cardiac stimulation device 100 may utilize the atrial and ventricular sensing circuits 144, 146 to sense cardiac signals, which can be analyzed to determine whether a particular cardiac rhythm is physiologic or pathologic. The timing intervals between sensed events (e.g., P-waves, R-waves, and T-waves) may be analyzed by an arrhythmia detection component (not shown) of the microcontroller 120 by, e.g., comparing the intervals to predefined rate zone limits (e.g., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (such as bradycardia pacing and, if applicable, anti-tachycardia pacing or cardioversion/defibrillation shocks).

Cardiac signals may, in addition to being applied to atrial and ventricular sensing circuits 144, 146, also be applied to inputs of an analog-to-digital (A/D) data acquisition system (not shown). The A/D data acquisition system is preferably configured to acquire intracardiac electrogram signals, convert the raw analog data into a digital signal, and store the digital data for later processing and/or telemetric transmission to an external device. The data acquisition system may be selectively coupled to various leads 107, 108 through the electronic configuration switch to allow sampling of cardiac signals across any desired pair of electrodes. Advantageously, the data acquisition system may be coupled to the microcontroller 120, or other detection circuitry, for detecting an evoked response from the heart in response to an applied stimulus, thereby aiding in the detection of "capture." Capture occurs when an electrical stimulus applied to the heart is of sufficient energy to depolarize the cardiac tissue, thereby causing the heart muscle to contract. The microcontroller 120 generally detects a depolarization signal during a window following a stimulation pulse, the presence of which indicates that capture has occurred. The microcontroller 120 enables capture detection by triggering the ventricular pulse generator 124 to generate a stimulation pulse, starting a capture detection window using the timing control circuitry within the pacing subsystem 130 and/or microcontroller 120, and enabling the data acquisition system to sample the cardiac signal that falls in the capture detection window and, based on the amplitude or other indicia, determines if capture has occurred.

Capture detection may occur on a beat-by-beat basis or on a sampled basis. A capture threshold search can be performed at regular intervals—e.g., once a day during at least the acute phase (e.g., the first 30 days after implantation) and less frequently thereafter. A capture threshold search procedure begins at a desired starting point (e.g., a high energy level, or else the level at which capture is currently occurring) and decreases the energy level until capture is lost. The value at which capture is lost is known as the capture threshold. Thereafter, a safety margin may be added to the capture threshold to arrive at a pacing stimulus energy value.

Programmable operating parameters may be stored in the memory of the microcontroller 120 and/or pacing subsystem 130 and modified, as required, in order to customize the operation of the implantable cardiac stimulation device 100 to suit the needs of a particular patient. Such operating parameters may define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 102 within each therapy. The memory is preferably large enough to store a relatively large amount of data (e.g., from the data acquisition system), which may be read out at a later time (by telemetry) and used for subsequent analysis to guide the programming of the device.

The operating parameters of the implantable cardiac stimulation device 100 may advantageously be programmed noninvasively through a telemetry circuit 164 in telemetric communication with an external programming device (not shown), such as a programmer, transtelephonic transceiver, or a diagnostic system analyzer. The microcontroller 120 preferably controls activation and operation of the telemetry circuit 164, through which intracardiac electrograms (ECGs) and status information relating to the operation of the implantable cardiac stimulation device 100 can be sent to the external programming device.

In the case where the implantable cardiac stimulation device 100 is intended to be a part of an implantable cardioverter/defibrillator (ICD) device, high voltage shocking circuit may be provided under control of the microcontroller 120. The shocking circuit may be programmed to generate shock pulses of different selectable energy magnitudes—for example, of low (up to 0.5 joules), moderate (0.5-10 joules), or high energy (11 to 40 joules). Cardioversion shocks tend to be of low to moderate energy level (so as to minimize pain felt by the patient), and may be synchronized with an R-wave. Cardioversion therapy tends to be utilized, generally, for the treatment of tachycardia. Defibrillation shocks are generally of moderate to high energy level (e.g., in the range of 5-40 joules), delivered synchronously or asynchronously (since R-waves may be too disorganized during a fibrillation episode). Defibrillation shocks are generally utilized for treating fibrillation.

According to a preferred embodiment, the implantable cardiac stimulation device 100 includes, among the pacing parameters 132 which determine the operation of the pacing subsystem 130, a post-ventricular atrial blanking interval value 135 ("PVAB sense") associated with ventricular sense events and a post-ventricular blanking interval value 136 ("PVAB pace") associated with ventricular pace events. The PVAB sense interval value 135 and PVAB pace interval value 136 are preferably stored in erasable memory (such as RAM), either volatile or non-volatile. With each ventricular event, the pacing subsystem 130 preferably selects either the PVAB sense interval value 135 or the PVAB pace interval value 136 for timing the post-ventricular atrial blanking interval following the ventricular event. Both the PVAB sense interval value 135 and the PVAB pace interval value 136 may be selected by a physician or programmer via the remote interface 164. A set of acceptable discrete values 167 may be provided from which the PVAB sense interval value 135 or PVAB pace interval value 136 can be selected. In addition, as described in more detail hereafter, a search routine 169 may be executed by the microcontroller 120 for systematically applying the discrete atrial blanking period interval values 167 and monitoring whether far-field R-waves are detected after expiration of each applied atrial blanking period interval value. Alternatively, the search routine and discrete values may reside in an external programmer, with control and feedback (A-sense and V-sense) signals passed to and from the implanted device via the telemetry interface 166.

Figure 2:
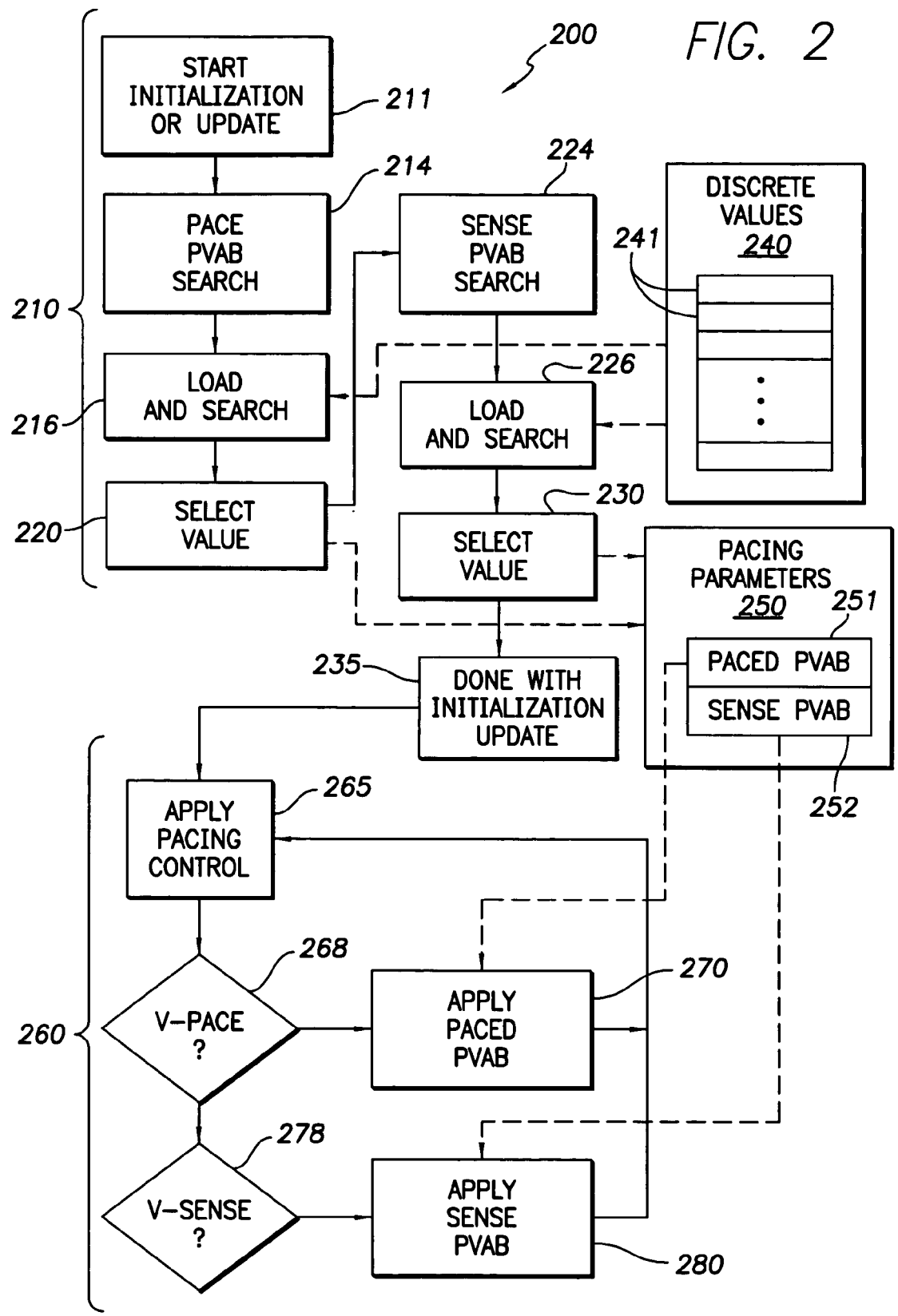
FIG. 2 is a process flow chart illustrating the programming and utilization of different post-ventricular atrial blanking intervals.

FIG. 2 is a flow chart illustrating a process 200 for programming and utilizing different post-ventricular atrial blanking intervals as may be employed, for example, in the implantable cardiac stimulation device 100 of FIG. 1 or another cardiac stimulation device. While the steps in FIG. 2 will be described with reference to the implantable cardiac stimulation device 100 of FIG. 1, it should be understood that the steps may be used in other devices as well. Moreover, the order of various steps in FIG. 2 may be varied based upon preference. As illustrated in FIG. 2, the process 200 starts at step 211, wherein the implantable cardiac stimulation device 100 is initialized or else instructed to commence a blanking interval search routine. The process 200 may be initiated at time of implantation or at a subsequent clinical visit by the patient, or automatically by the device itself according to a pre-programmed schedule or in response to certain detected conditions.

In the next step 214, the implantable cardiac stimulation device 100 or, alternatively, an external programmer initiates a search routine to determine a post-ventricular atrial blanking (PVAB) interval to be used with paced ventricular events. The search routine may be conducted, for example, according to the steps shown in FIG. 3 or 4, described hereinafter. Accordingly, as indicated in step 216, various discrete values (as indicated by, e.g., discrete values 241 in FIG. 2 or 167 in FIG. 1) may be sequentially loaded into the pacing subsystem 130, until a suitable blanking interval is determined. If the search routine is being conducted via an external programmer, the discrete values may be communicated to the search routine 169 via the remote interface 164. When a suitable blanking interval has been determined, the PVAB interval for paced ventricular events is selected, as indicated by step 220, and loaded into the active pacing parameters 250 (corresponding to pacing parameters 132 in FIG. 1) as paced PVAB interval 251.

The process 200 then moves to step 224, whereupon the implantable cardiac stimulation device 100 or, alternatively, an external programmer initiates a search routine to determine a post-ventricular atrial blanking (PVAB) interval to be used with sensed ventricular events. The search routine may be conducted, for example, according to the steps shown in FIG. 3 or 4, described hereinafter. Accordingly, as indicated in step 226, various discrete values may be sequentially loaded into the pacing subsystem 130, until a suitable blanking interval is determined. The discrete values may differ from those used for the PVAB interval associated with paced ventricular events, because the expected conduction time for far-field R-waves differs between sensed and paced events. The discrete values may be resident in the implantable cardiac stimulation device 100 or, if the routine is being conducted via an external programmer, they may be communicated to the search routine 169 via the remote interface 164. Following step 226, the PVAB interval for sensed ventricular events is selected, as indicated by step 230, and loaded into the active pacing parameters 250 as sense PVAB interval 252.

Alternatively, rather than forcing a PVAB interval search for paced events at a given time and a separate PVAB interval search for sensed events at a given time, the process 200 may simply take the type of cardiac activity as it occurs naturally with the patient. Thus, when the cardiac stimulation device generates a pacing pulse, the cycle is associated with the search routine for a pace PVAB interval and the appropriate test PVAB interval for paced events is applied, whereas if the cardiac stimulation device detects a natural ventricular event, the cycle is associated with the search routine for a sense PVAB interval and the appropriate test PVAB interval for sensed events is applied. In this manner, the tests for separate pace and sense PVAB intervals can be carried out simultaneously along two different threads, intermixed among different cardiac cycles. In addition, the physician may be provided the ability to disable one or the other PVAB tests (i.e., either the sense or pace PVAB interval test), or to force one or the other PVAB test regardless of the order in which the process 200 would otherwise employ the tests.

After both the paced PVAB interval 251 and the sense PVAB interval 252 have been selected, the initialization or update process associated with the blanking intervals is completed, as indicated by step 235. The process 200 then moves to a pacing control routine 260, a portion of which is illustrated in FIG. 2.

In the pacing control routine 260, the implantable cardiac stimulation device 100 applies its normal programmed pacing algorithm according to the selected pacing mode (e.g., VDD, DDD, etc.), as modified by the subsequent steps in FIG. 2. Upon the occurrence of a ventricular event, the implantable cardiac stimulation device 100 employs an atrial blanking interval dependent upon whether the ventricular event was sensed or paced. If the ventricular event was a paced event, then the process 200 moves from step 268 to step 270, whereupon the paced PVAB interval 251 is applied by the pacing subsystem 130. If, on the other hand, the ventricular event was a sensed event, then the process 200 moves from step 278 (which may be omitted if it is assumed that a non-paced ventricular event must be a sensed event) to step 280, whereupon the sense PVAB interval 252 is applied by the pacing subsystem 130. The process 200 then returns to step 265, whereupon the pacing subsystem 130 continues to apply its normal pacing control routine. In this manner, the implantable cardiac stimulation device 100 provides different post-ventricular atrial blanking intervals based upon the type of ventricular activity, and integrates the different atrial blanking intervals into its pacing regimen.

Figure 3:
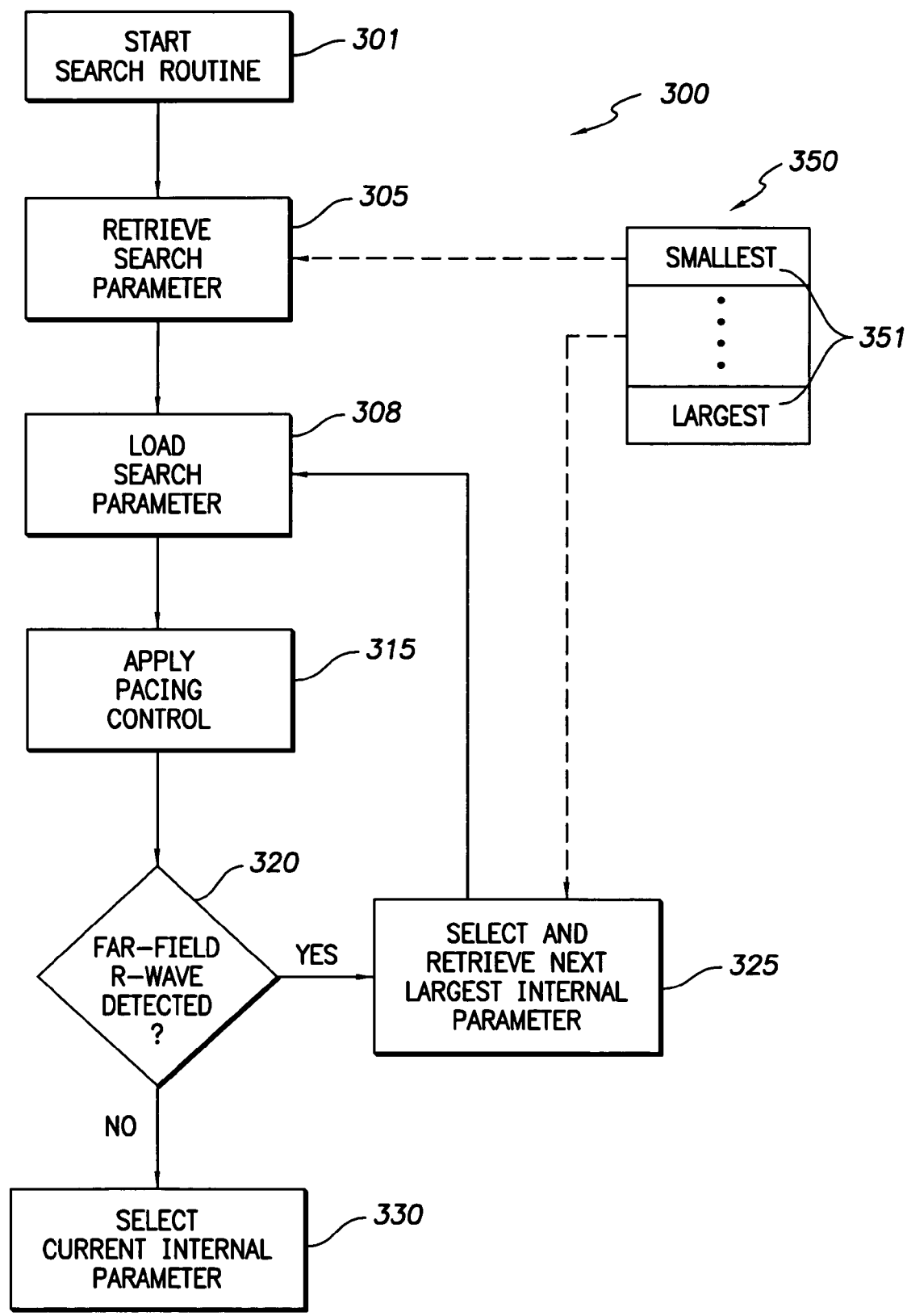
FIG. 3 is a process flow chart for automated determination of an atrial blanking interval in accordance with one embodiment.
Figure 4:
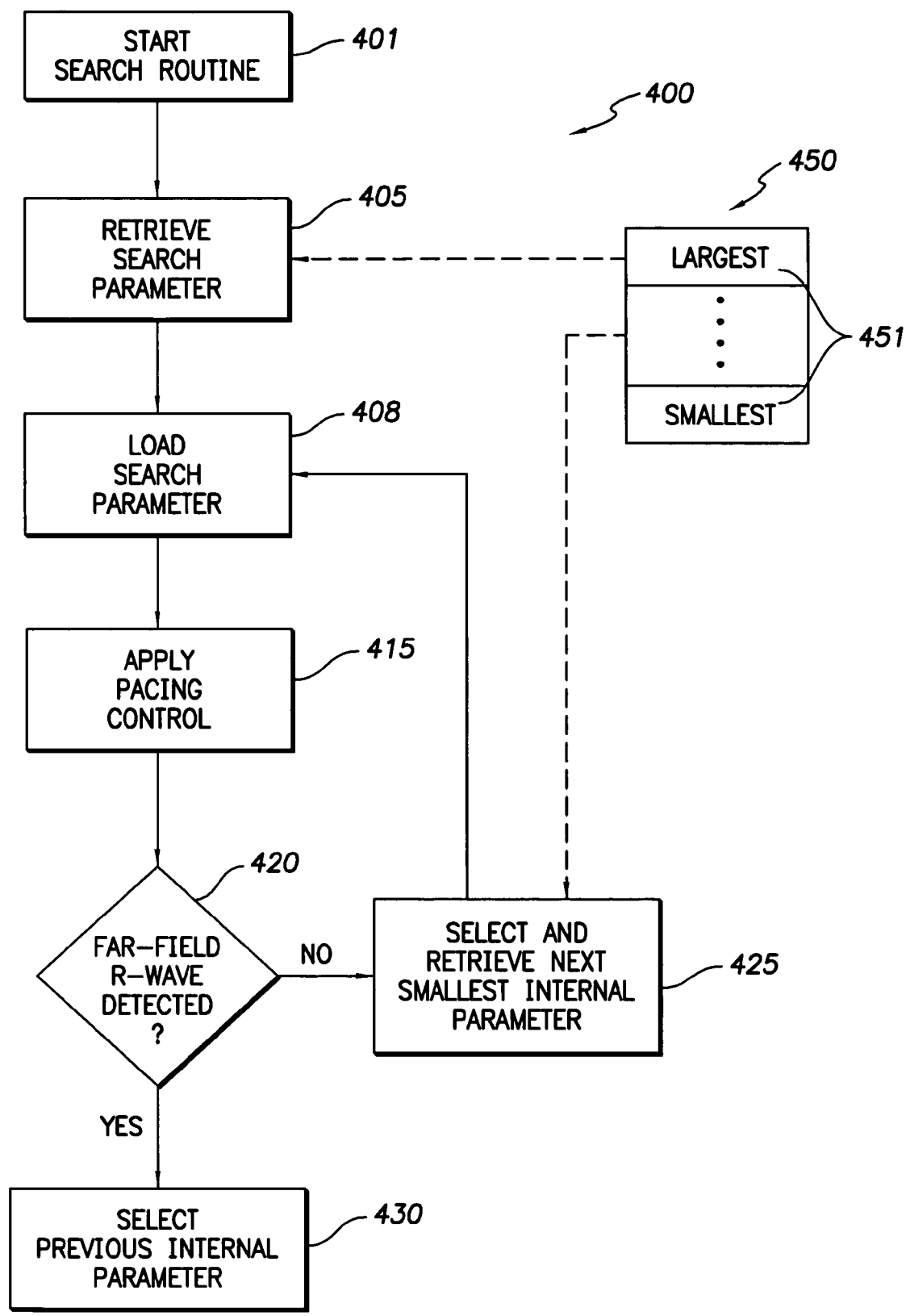
FIG. 4 is a process flow chart for automated determination of an atrial blanking interval in accordance with another embodiment.

FIGS. 3 and 4 are flow charts illustrating examples of different automated techniques for determination of an atrial blanking interval as may be employed, for example, in the process 200 of FIG. 2 or another process utilized by a cardiac stimulation device. In the example illustrated in FIG. 3, the search routine starts execution in step 301. As illustrated next in step 305, the search routine causes the first search parameter to be retrieved. In the implantable cardiac stimulation device 100 of FIG. 1, for example, the first search parameter, as well as subsequent search parameters, may be retrieved from the set of discrete values 167 accessible to the microcontroller 120 or passed to the implantable cardiac stimulation device 100 from an external programmer via the remote interface 164. Discrete values 351 stored in a portion of memory 350 of the cardiac stimulation device or of the external programmer represent the discrete values which are utilized in the search routine. The discrete values 351 may represent all or some of the possible values which the post-ventricular atrial blanking interval may take on. If the discrete value 351 are resident in the implantable cardiac stimulation device 100, then preferably, through remote programming operations (via, e.g., remote interface 164 in the FIG. 1 embodiment), a physician or programmer may program upper and/or lower limits that the search routine may use for the post-ventricular atrial blanking interval. Therefore, the discrete values 351 available to the search routine may be fewer than all possible values for the post-ventricular atrial blanking interval. Alternatively, as opposed to a set of discrete values 351, the memory 350 may merely store starting and ending search values and an interval step value by which the search routine 300 gradually and incrementally steps until finding a suitable post-ventricular atrial blanking interval.

Figure 7:
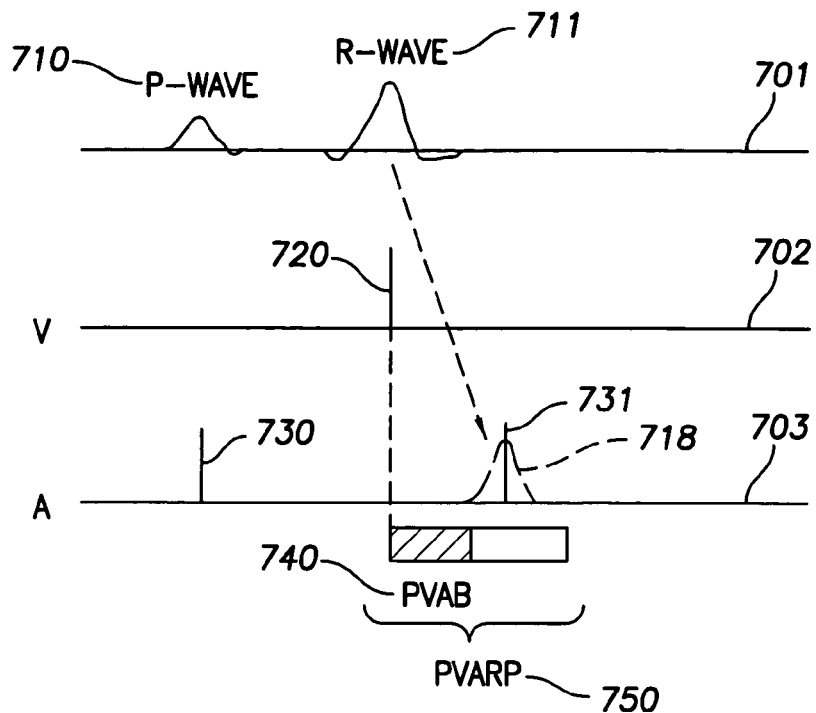
FIGS. 7 and 8 are graphs illustrating a search routine for determining an appropriate post-ventricular atrial blanking interval.
Figure 8:
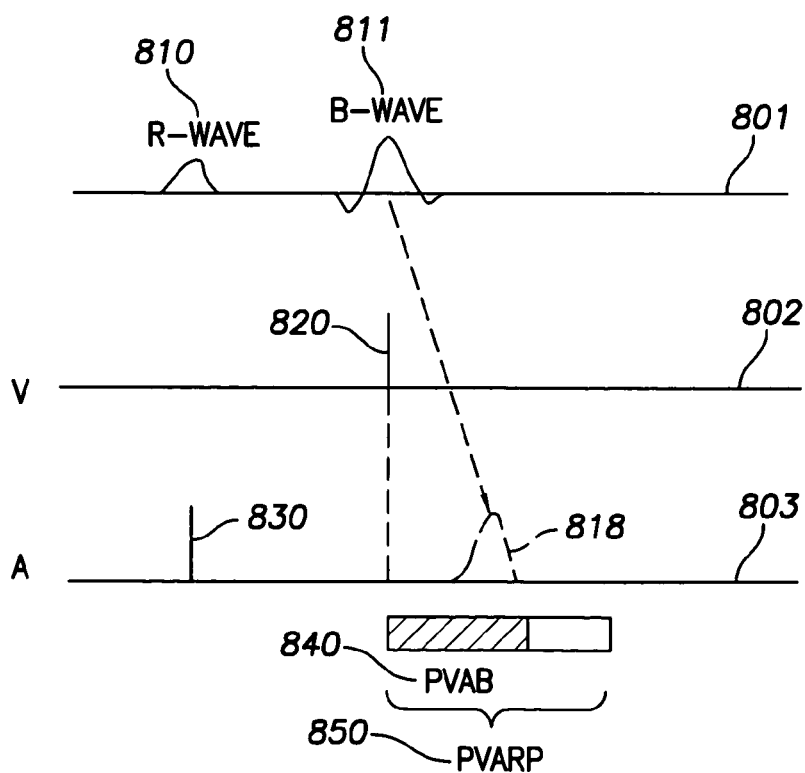

In the example of FIG. 3, the first search parameter is the smallest of the discrete values 351 available for the search routine. The first search parameter is loaded by the implantable cardiac stimulation device to be used as an active pacing parameter (for example, as one of the pacing parameters 132 used in the pacing subsystem 130, in the FIG. 1 implantable cardiac stimulation device). In a next step 315, the implantable cardiac stimulation device conducts pacing control as it normally would, but using the search parameter temporarily in place of the previous post-ventricular atrial blanking interval. Following the occurrence of a ventricular event, the implantable cardiac stimulation device times out the post-ventricular atrial blanking interval, during which time the atrial detection circuitry (e.g., atrial detection circuit 144) is rendered inactive, or its output is ignored. Following the post-ventricular atrial blanking interval, the implantable cardiac stimulation device attempts to detect a far-field R-wave (using, e.g., detection circuit 141 and techniques for sensing R-waves well understood in the art). The far-field R-wave may occur either in a post-ventricular atrial refractory period (PVARP) or later. The post-ventricular atrial refractory period, or PVARP (examples of which are illustrated in FIGS. 7 and 8), is generally a period following a ventricular event during which the occurrence of atrial events will not cause a paced response by the device. However, during the PVARP, and unlike during the post-ventricular atrial blanking interval, the atrial detection circuitry is active and atrial events (such as P-waves or far-field R-waves) can be detected, counted, and utilized in various internal therapeutic analyses. The PVARP commonly includes the post-ventricular atrial blanking interval as one of its constituent components. FIG. 7, explained in more detail below, illustrates the situation where a far-field R-wave is detected during the PVARP 750.

Detection of far-field R-waves may be accomplished in any of a variety of manners. As one example, a far-field R-wave detection window may be defined following the PVAB interval. If an atrial event is detected during the far-field R-wave detection window, then that event may be flagged as a far-field R-wave, or at least a potential far-field R-wave that may be further examined or utilized in connection with additional logic or means (e.g., morphology discrimination, or other techniques described below) for determining whether the event represents a true far-field R-wave. The far-field R-wave detection window may be fixed or programmable in nature.

Figure 9:
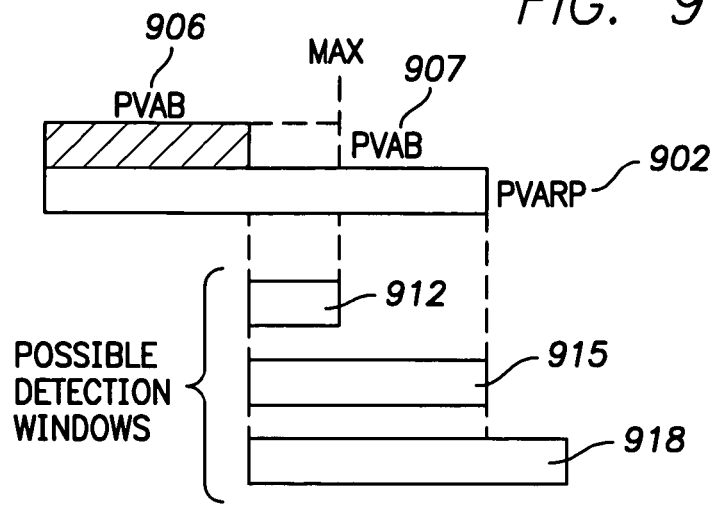
FIG. 9 is a diagram illustrating possible detection windows that may be applied in a search routine such as in FIG. 7 or 8.

Examples of possible far-field R-wave detection windows are illustrated in FIG. 9. There, a PVAB interval 906 is illustrated relative to an overall post-ventricular atrial refractory period (PVARP) interval 902. In some embodiments, the PVARP may be defined as or deemed to be the period following the end of the PVAB interval 906, but for the purposes of the present example the PVARP interval 902 will be described as starting at the same time as the PVAB interval 906. FIG. 9 illustrates three possible far-field R-wave detection windows 912, 915 and 918. The first far-field R-wave detection window 912 is chosen to end at the maximum selectable PVAB interval 907, so that the window 912 is defined as the period from the end of the selected PVAB interval 906 to the end of the maximum selectable PVAB interval 907. The second possible far-field R-wave detection window 915 is defined as the period from the end of the selected PVAB interval 906 to the end of the programmed or selected PVARP interval 902. The third possible far-field R-wave detection window 918 has a duration independent of the maximum PVAB interval 907 or the PVARP interval 902, and can generally be any duration subject to fixed or programmable limits in the cardiac stimulation device. As an example, an independent far-field R-wave detection window 918 may be set or programmed to, e.g., 100 or 150 milliseconds.

In any of the foregoing examples described in connection with FIG. 9, a minimum far-field R-wave detection window interval may be defined, such that the far-field R-wave detection window may not be less than the minimum window interval. Thus, for example, if the PVAB interval 906 is programmed or selected to be at or close to the maximum PVAB interval 907, the minimum far-field R-wave detection window interval will force the far-field R-wave detection window to be at least the minimum duration. The minimum far-field R-wave detection window interval, like other parameters, may be fixed or programmable in nature.

Even with a far-field R-wave detection window, there may be various challenges to accurate detection of far-field R-waves, and thus it may be desirable in certain embodiments to provide additional verification means to ensure that a detected phenomenon perceived by the cardiac stimulation device as far-field R-waves are actually such. One potential problem is that isolated premature atrial contractions (PACs) during a PVAB interval search may be misinterpreted as a far-field R-wave and cause a false positive detection. Such an event would tend to cause the PVAB interval to be set longer than necessary, although this would not necessarily pose any major danger to the patient. A subsequent execution of the PVAB interval search routine would likely adjust the PVAB interval to a more suitable duration. Because of the possibility of PACs, a scan of long to short PVAB intervals in the search routine, as described with respect to the alternative embodiment illustrated in FIG. 4, may be preferred. A persistent bigeminal atrial rhythm may also occur and lead to a false positive detection of a perceived far-field R-wave. In such a case, it may nonetheless be desirable, in the absence of an algorithm to specifically identify this type of rhythm, to cover the twin atrial beat with a longer PVAB interval, and so there may actually be a benefit to the patient in allowing bigeminal atrial activity to be detected in the far-field R-wave detection window and used to set a longer PVAB interval than otherwise might be employed.

In order to eliminate or minimize false positives caused by PACs, the search routine 300, and in particular step 320 thereof, may be implemented such that far-field R-waves are required to be detected over some number of cycles (either X consecutive cycles, or X out of Y cycles, where X and/or Y may be fixed or programmable parameters) at a particular PVAB interval setting before being deemed indicative of true far-field R-wave events. While this technique may prevent isolated PACs from causing a false positive far-field R-wave detection, it may still not detect a persistent bigeminal rhythm, which can potentially be dealt with in other manners or else simply treated the same as far-field R-waves. It may be desirable, during the search routine 300 or step 320 thereof, to disable atrial tachycardia detection to avoid detection of several consecutive potential far-field R-waves from triggering a false atrial tachycardia detection.

If the far-field R-wave is detected (or a sufficient number of far-field R-waves are detected over a given number of cycles), then the implantable cardiac stimulation device has sufficient information to conclude that the blanking interval is too short, and may therefore be lengthened. Accordingly, in a next step 325, the search routine causes the next search parameter from discrete values 351 stored in memory 350 to be retrieved. In the example of FIG. 3, the search parameter retrieved in step 325 is the next largest of the discrete values 351 available for the search routine. The retrieved search parameter is loaded by the implantable cardiac stimulation device to be used as an active pacing parameter and, in step 315; the implantable cardiac stimulation device conducts pacing control as it normally would, but temporarily using the current search parameter for the post-ventricular atrial blanking interval. Following the occurrence of a ventricular event, the implantable cardiac stimulation device times out the post-ventricular atrial blanking interval, during which time the atrial detection circuitry (e.g., atrial detection circuit 144) is rendered inactive. As before, following the post-ventricular atrial blanking interval, the implantable cardiac stimulation device attempts to detect a far-field R-wave, as indicated by step 320. If a far-field R-wave is detected (or a sufficient number of far-field R-waves are detected over a given number of cycles), then the search routine process 300 returns to step 325, selects the next largest search parameter, and continues with the search loop until the post-ventricular atrial refractory interval is long enough such that a far-field R-wave is not detected following a ventricular event.

Once the test in step 320 is satisfied (i.e., a far-field R-wave is not detected following the temporarily selected post-ventricular atrial blanking interval, or a similar far-field R-wave detection test is negative), the search routine process 300 moves to step 330, whereupon the implantable cardiac stimulation device selects the temporary search parameter or a derivative thereof for use in its pacing subsystem on an ongoing basis. As an example of a derivative of the search parameter, the implantable cardiac stimulation device may add a safety margin (e.g., 10 milliseconds or any other suitable value) to the temporary search parameter prior to loading it in the pacing subsystem for use on an ongoing basis. The post-ventricular atrial blanking interval to be used for ongoing pacing control is therefore based upon the last used temporary search parameter. In the context of the device 100 illustrated in FIG. 1, the temporary search parameter (or derivative thereof) is loaded into the pacing parameters 132 as either the PVAB sense interval value 135 or PVAB pace interval value 136, as the case may be. The search routine process 300 may be run twice, once each for the PVAB sense interval value 135 and the PVAB pace interval value 136, or may be run in parallel for both.

FIGS. 7 and 8 illustrate an example of operation of the search routine process 300 in FIG. 3. In FIGS. 7 and 8, the first plots 701, 801 indicate waveforms corresponding to cardiac activity, the second plots 702, 802 illustrate the ventricular channel, and the third plots 703, 803 illustrate the atrial channel. FIG. 7 illustrates the situation where the selected post-ventricular atrial blanking interval 740 is too short, such that a far-field R-wave 718 is detected after the post-ventricular atrial blanking interval 740. In the particular example of FIG. 7, a natural P-wave 710 results in a detected atrial event 730, followed by a natural R-wave 711 that results in a sensed ventricular event 720, followed by a far-field R-wave 718 detected on the atrial channel and registering as event 731 during the post-ventricular atrial refractory period (PVARP) 750 but after the post-ventricular atrial blanking (PVAB) interval 740.

FIG. 8 illustrates another example, but where the post-ventricular atrial blanking (PVAB) interval 840 has been lengthened according to, e.g., a search routine such as illustrated in FIG. 3. In this example, following a natural P-wave 810, the subsequent R-wave 811 leads to a far-field R-wave 818 that would ordinarily be detected on the atrial channel. However, the lengthened PVAB interval 840 prevents the far-field R-wave 818 from being detected. Assuming that PVAB intervals 740 and 840 are successive discrete values in the search routine 300, PVAB interval 840 could be selected as the basis for the ongoing post-ventricular atrial blanking interval used in connection with sensed ventricular events. A separate search routine may be carried out to determine the ongoing post-ventricular atrial blanking interval to be used in connection with paced ventricular events.

FIG. 4 illustrates an alternative search routine process 400, which is conceptually similar to the process 300 described with respect to FIG. 3. In the FIG. 4 process 400, however, the post-ventricular atrial blanking interval is determined using a search routine which starts with larger values and gradually diminishes the values until a suitable post-ventricular atrial blanking interval is found. Thus, in a first step 401 of the process 400 of FIG. 4, the search routine starts execution. As illustrated next in step 405, the search routine causes the first search parameter to be retrieved. As described before, in the implantable cardiac stimulation device 100 of FIG. 1, the first search parameter, as well as subsequent search parameters, may be retrieved from the set of discrete values 167 accessible to the microcontroller 120. Discrete values 451 stored in a portion of memory 450 of the cardiac stimulation device represent the discrete values which are utilized in the search routine. The discrete values 451 may represent all or some of the possible values which the post-ventricular atrial blanking interval may take on. Preferably, through remote programming operations (via, e.g., remote interface 164 in the FIG. 1 embodiment), a physician or programmer may program upper and/or lower limits that the search routine may use for the post-ventricular atrial blanking interval. Alternatively, as opposed to a set of discrete values 451, the memory 450 may merely store starting and ending search values and an interval step value by which the search routine 400 gradually decrements until finding a suitable post-ventricular atrial blanking interval.

In the example of FIG. 4, the first search parameter is the largest of the discrete values 451 available for the search routine. As indicated by step 408, the first search parameter is loaded by the implantable cardiac stimulation device to be used as an active pacing parameter (for example, as one of the pacing parameters 132 used in the pacing subsystem 130, in the FIG. 1 implantable cardiac stimulation device). In a next step 415, the implantable cardiac stimulation device conducts pacing control as it normally would, but using the search parameter temporarily in place of the previous post-ventricular atrial blanking interval. Following the occurrence of a ventricular event, the implantable cardiac stimulation device times out the post-ventricular atrial blanking interval, during which time the atrial detection circuitry (e.g., atrial detection circuit 144) is rendered inactive. Following the post-ventricular atrial blanking interval, the implantable cardiac stimulation device attempts to detect a far-field R-wave (using, e.g., detection circuit 141). The far-field R-wave may occur either in a post-ventricular atrial refractory period (PVARP) or later, and may be detected within a far-field R-wave detection window as previously described, for example, in connection with FIG. 9. If the far-field R-wave is not detected, then the implantable cardiac stimulation device has sufficient information to conclude that the blanking interval may be too long, and therefore a shorter interval may be tested.

As previously described with respect to FIG. 3, certain additional logic or means may be employed to avoid false detection of activity other than far-field R-waves as satisfying step 420. For example, detection of far-field R-waves may need to occur over a certain number of cycles (e.g., either X consecutive cycles, or X of Y cycles) in order for the presence of far-field R-waves to be confirmed. Other techniques, such as morphology discrimination, may also be used. Also as previously described with respect to FIG. 3, it may be desirable, during the search routine 400 or step 420 thereof, to disable atrial tachycardia detection to avoid detection of several consecutive potential far-field R-waves from triggering a false atrial tachycardia detection.

In a next step 425, the search routine causes the next search parameter from discrete values 451 stored in memory 450 to be retrieved. In the example of FIG. 4, the search parameter retrieved in step 425 is the next largest of the discrete values 451 available for the search routine. The retrieved search parameter is loaded by the implantable cardiac stimulation device, as indicated by step 408, to be used as an active pacing parameter and, in step 415, the implantable cardiac stimulation device conducts pacing control as it normally would, but temporarily using the current search parameter for the post-ventricular atrial blanking interval. Following the occurrence of a ventricular event, the implantable cardiac stimulation device again times out the post-ventricular atrial blanking interval, during which time the atrial detection circuitry (e.g., atrial detection circuit 144) is rendered inactive. As before, following the post-ventricular atrial blanking interval, the implantable cardiac stimulation device attempts to detect a far-field R-wave, as indicated by step 420. If no far-field R-wave is detected, then the search routine process 400 returns to step 425, selects the next largest search parameter, and continues with the search loop until the post-ventricular atrial refractory interval is short enough such that a far-field R-wave is detected following a ventricular event.

Once the test in step 420 is satisfied (i.e., a far-field R-wave is detected following the temporarily selected post-ventricular atrial blanking interval), the search routine process 400 moves to step 430, whereupon the implantable cardiac stimulation device selects the previous temporary search parameter or a derivative thereof for use in its pacing subsystem on an ongoing basis. The previous temporary search parameter is selected because it was the last search parameter that was long enough to prevent detection of a far-field R-wave. Thus, if the last three search parameters were 80 milliseconds (no far-field R-wave), 70 milliseconds (no far-field R-wave), and 60 milliseconds (far-field R-wave detected), the search routine 400 would select 70 milliseconds as the search parameter on which to base the new post-ventricular atrial refractory interval. As before, the implantable cardiac stimulation device may add a safety margin (e.g., 10 milliseconds or any other suitable value) to the temporary search parameter prior to loading it in the pacing subsystem for use on an ongoing basis. In the context of the device 100 illustrated in FIG. 1, the temporary search parameter (or derivative thereof) is loaded into the pacing parameters 132 as either the PVAB sense interval value 135 or PVAB pace interval value 136, as the case may be. The search routine process 400 may be run twice, once each for the PVAB sense interval value 135 and the PVAB pace interval value 136, or may be run in parallel for both.

In certain embodiments, it may be desirable to provide an initial screening test (which may be triggered and run in an automated manner) prior to executing a search routine such as that of FIG. 3 or 4, for the purpose of, e.g., either suppressing execution of the search routine or else assisting selection of which of alternative searches shown in FIGS. 3 and 4 should be utilized. An example of a screening test might be to determine whether far-field R-waves are presently being detected. A variety of factors may influence detection of far-field R-waves, including such things as the posture or activity of the patient (which may, for example, cause changes in lead and/or heart muscle orientation). Generally, in the absence of far-field R-waves or other abnormal cardiac activity (such as atrial bigeminy), the average atrial rate should be approximately the same as the average ventricular rate. If far-field R-waves are being detected, then it would be expected that the atrial rate would be approximately twice the ventricular rate. The screening test may thus involve measurement of an average atrial rate and average ventricular rate. If the average atrial rate is approximately equal to the average ventricular rate, then a downward search starting with longer test PVAB intervals (i.e., the FIG. 4 test) would be used, whereas if the average atrial rate is approximately twice the average ventricular rate, then, since far-field R-waves are possibly present, an upward search starting with shorter test PVAB intervals (i.e., the FIG. 3 test) would be used.

Alternatively, if the average atrial rate is approximately twice the average ventricular rate, it is possible that an atrial bigeminy rhythm is present. In such a case, the physician may choose not to have the search routine operate. Nonetheless, the implantable cardiac stimulation device may store the ECG for later diagnostic purposes.

In a practical implementation, the logic of the search process used in the implantable cardiac stimulation device may employ a programmable threshold in connection with measured average atrial and ventricular rates for determining whether far-field R-waves are present and thus for determining which type of search to employ or whether to suppress the search altogether. As an example, the implantable cardiac stimulation device may compare the average atrial rate to the average ventricular rate using a formula such as the following:

$$A_{AVG} < k \cdot V_{AVG}$$

where $A_{AVG}$ represents the average atrial rate, $V_{AVG}$ represents the average ventricular rate, and k represents a selected constant (e.g., 1.5). If the above condition is met—in other words, if $A_{AVG}$ is less than k multiplied by $V_{AVG}$—then far-field R-waves are deemed generally not present and a downwards search routine (as in FIG. 4) is employed. If, on the other hand, the above condition is not met, then far-field R-waves are deemed generally present and an upwards search routine (as in FIG. 3) is employed, or else the search routine is suppressed, depending upon the physician's preference as expressed in the programmed search parameters.

Because far-field R-waves may come and go, depending upon various conditions and factors, the aforementioned screening test may be run periodically to detect if far-field R-waves are present. If a relatively short PVAB interval has been selected based upon the assumption that far-field R-waves are not present due to conditions present at the time the PVAB search routine was run, then the periodic screening test may detect the return or commencement of far-field R-waves, and may signal to the control logic of the implantable cardiac stimulation device that a new or updated PVAB search routine needs to be run. Likewise, the periodic far-field R-wave screening test may detect when far-field R-waves have subsided, thereby providing a suitable condition for running a PVAB interval search routine, so long as far-field R-waves are periodically monitored thereafter to ensure that they have not returned.

Likewise, it may be desirable for the implantable device to be generally programmed to detect when the detected atrial rate exceeds the ventricular rate. In such a situation, the selected PVAB intervals being utilized may not be correctly set, and the device may decide to trigger a new search routine. Similarly, if the atrial rate is unstable the device may decide to trigger a new search routine. Prior to initiating a new search routine, it is desirable to ensure that the device is not detecting atrial arrhythmia or other similar phenomenon.

In one aspect, an automated search routine employable in an implantable cardiac stimulation device is configured to adjust or optimize one or more post-ventricular atrial blanking intervals by, e.g., searching for an interval length that is longer than the conduction time for far-field R-waves. An automated search routine preferably adjusts, on a dynamic basis, pacing parameters that were originally determined or programmed at time of the device's implant or at one of the patient's follow-up clinical evaluations. The search routine process (such as shown in FIG. 3 or 4, for example) may be initiated according to a programmed schedule, may be run a predetermined time after implantation, and/or may be initiated in response to external instructions. For example, the search routine process may be run at or shortly after implantation, and then periodically thereafter according to a pre-set or programmable schedule. Alternatively, the process may be run only after certain diagnostic indicators occur indicating that detection of far-field R-waves may be causing aberrations in the processes carried out by the pacing subsystem, thus indicating the existing PVAB interval may be too short.

The processes described herein may be used in connection, in whole or part, with a variety of other related or unrelated techniques. As merely one example, the processes herein may be used in conjunction with techniques described in U.S. Pat. No. 6,477,416 B1 to Florio et al., which is hereby incorporated by reference as if set forth fully herein. In such an embodiment, either the paced or sensed PVAB interval described herein may be followed by a far-field interval (FFI) window as described in the aforementioned patent.

The various blanking interval adjustment techniques employed herein are particularly advantageous for an implantable cardiac stimulation device, of the type which commonly operates autonomously for extended periods of time, but may also find use in external devices such as programmers or external pacing equipment. As one example, a cardiac device programmer (e.g., a physician) may use the foregoing methods at time of implant, or a subsequent clinical visit, to measure or determine one or more appropriate post-ventricular atrial blanking intervals based upon the patient's response using different search parameters, and then select one or more PVAB intervals (e.g., different PVAB intervals for ventricular sense and pace events) in an implanted cardiac stimulation device to be used as ongoing pacing parameters. The physician or other appropriate individual may instruct the implantable cardiac stimulation device, via remote instructions, to initiate a blanking interval search routine and/or to increase or decrease the current blanking interval in specific incremental steps. The physician or operator may observe the patient's ECG on a monitor and determine whether or not far-field R-waves are detected. The programmer may provide a simple interface, e.g. a touchscreen button, by way of which the physician may indicate to the system whether or not far-field R-waves are present, as appropriate. When finished with the search routine, the physician or operator may instruct the implantable cardiac stimulation device to load the desired value for the blanking interval, and/or may freeze and print out the programmer screen illustrating the test results. Alternatively, an indication of the transition between successful detection and unsuccessful detection of far-field R-waves resulting from the ordered sequence of test values may be communicated to the implantable cardiac stimulating device from an external programmer, allowing the device to load the selected parameters in response thereto. In the foregoing manner (including the described variations), a semi-automatic test and search routine may be implemented in which the human operator may be involved with initiating the routine, assessing whether far-field R-waves are present or not (similar to step 320 in FIG. 3 or step 420 in FIG. 4), confirming the results, and allowing new paced and/or sense PVAB values (e.g., 251 and 252, respectively, illustrated in FIG. 2) to be loaded as active pacing parameters 250 in the storage of the implantable device.

Similarly, the physician may use a programmer or other external device to walk through the possible values of the post-ventricular atrial blanking interval using a remote connection with the implanted device. The physician may determine whether or not far-field R-waves are being sensed and select, via the remote interface, new test values accordingly.

In other embodiments where an external programmer or other external device are used to semi-automatically conduct a search for a suitable post-ventricular atrial blanking interval, the search logic and/or discrete test values may be stored in the external programmer or device. Test values or indicia selecting new test values may be selected by the search logic, or the physician operating the external device, and transmitted to the implantable cardiac stimulation device over a wireless link. In such an embodiment, the implantable cardiac stimulation device acts as a slave responsive to commands from the external programmer.

As one example of a semi-automated process, a physician (or other clinical operator) may first select, using an external programmer, whether to program the paced PVAB interval or sense PVAB interval. The physician may then be presented with programming options to force V-pacing or V-sensing as appropriate. The PVAB test values may be stored, for example, in the external programmer, and the implantable device is successively programmed with these values after the physician initiates the test routine. When the physician observes far field R-waves appear (or disappear if test values for the PVAB intervals go from short to long), then the physician may cause the test routine to end (e.g., by selecting an appropriate button on the external programmer). The external programmer may, if desired, label suspected far-field R-waves with special markers on the programmer's display. When the physician ends the test routine, an electrogram showing the last few seconds of the test appears on the programmer's display. The transition point between detection and non-detection of far-field R-waves may be automatically labeled by the external programmer, and the PVAB interval values before and after the transition may likewise be displayed. The suggested PVAB interval value may be presented on the display, and the physician or other operator asked for confirmation. Upon confirmation, the external programmer programs the implantable device with the suggested PVAB interval value for use on a long-term basis (until re-programmed manually or, for example, through an automated search routine as described elsewhere herein). The physician may program both the paced and sense PVAB interval values in this manner.

Figure 10:
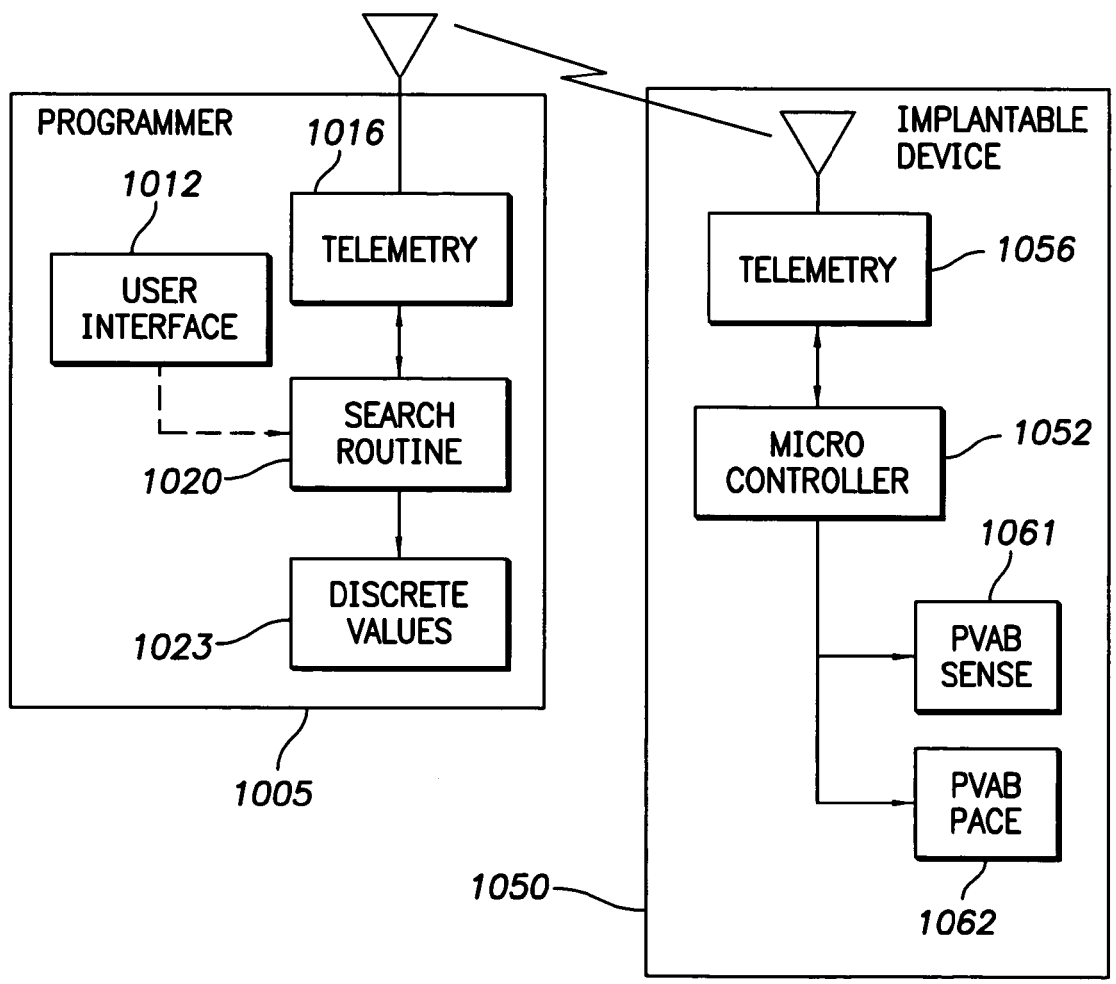
FIG. 10 is a diagram of an embodiment in which the search routine is resident in an external programmer interfacing with an implantable device through a telemetry link.

An example of an embodiment utilizing an external programmer is illustrated in the functional block diagram of FIG. 10. As shown therein, an external programmer 1005 is provided with a telemetry interface 1016 for communicating with an implantable cardiac stimulation device 1050. The external programmer 1005 includes a PVAB search routine 1020 comprised of executable software instructions. The PVAB search routine 1020 may be invoked via any standard user interface 1012 of the external programmer 1005. The search routine 1020 may operate according to the general steps illustrated in FIGS. 3 and/or 4. It may, for example, draw upon discrete values 1023 stored in the external programmer 1005, and/or receive physician-selected test PVAB interval values through the user interface 1012. The external programmer 1005 then downloads the test PVAB intervals, either in one or more groups or individually, to the implantable cardiac stimulation device 1050 for use in the PVAB search process. The implantable cardiac stimulation device 1050 receives the test PVAB interval(s) via its telemetry interface 1056, and provides them to microcontroller 1052. The implantable cardiac stimulation device 1050 then utilizes the test PVAB interval(s) in operation.

The implantable cardiac stimulation device 1050 may perform detection of far-field R-waves by itself and relay the information to the external programmer 1005 via the telemetry interface 1056. A physician may monitor the patient's cardiac activity on a display or printed graph at the external programmer 1005. Information relayed by the device regarding device-detected far-field R-waves may be used to label the corresponding events as such on the display or on the printed graph, thus aiding the physician in deciding whether or not far-field R-waves are present. Alternatively, this information may be used directly by the programmer in deciding how to proceed with the search, e.g. in decision steps 320 in FIG. 3 or 420 in FIG. 4. The search routine 1020 may be configured to automatically walk through the discrete values 1023 until a suitable PVAB interval is selected (or separate suitable pace and sense PVAB intervals are selected, if that is the goal), or else the physician may manually walk through or override the PVAB intervals available to the search routine 1020. Ultimately, either through a fully or semi-automated search carried out through collaboration between the external programmer 1005 and the implantable cardiac stimulation device 1050, the desired PVAB interval(s) can be determined or selected. In the instant example, the finally selected sense PVAB interval 1061 and pace PVAB interval 1062 may be stored in the implantable cardiac stimulation device 1050 for ongoing use by the implantable device.

In yet other embodiments, the PVAB search routine may be implemented entirely in an external cardiac stimulation device.

Figure 11:
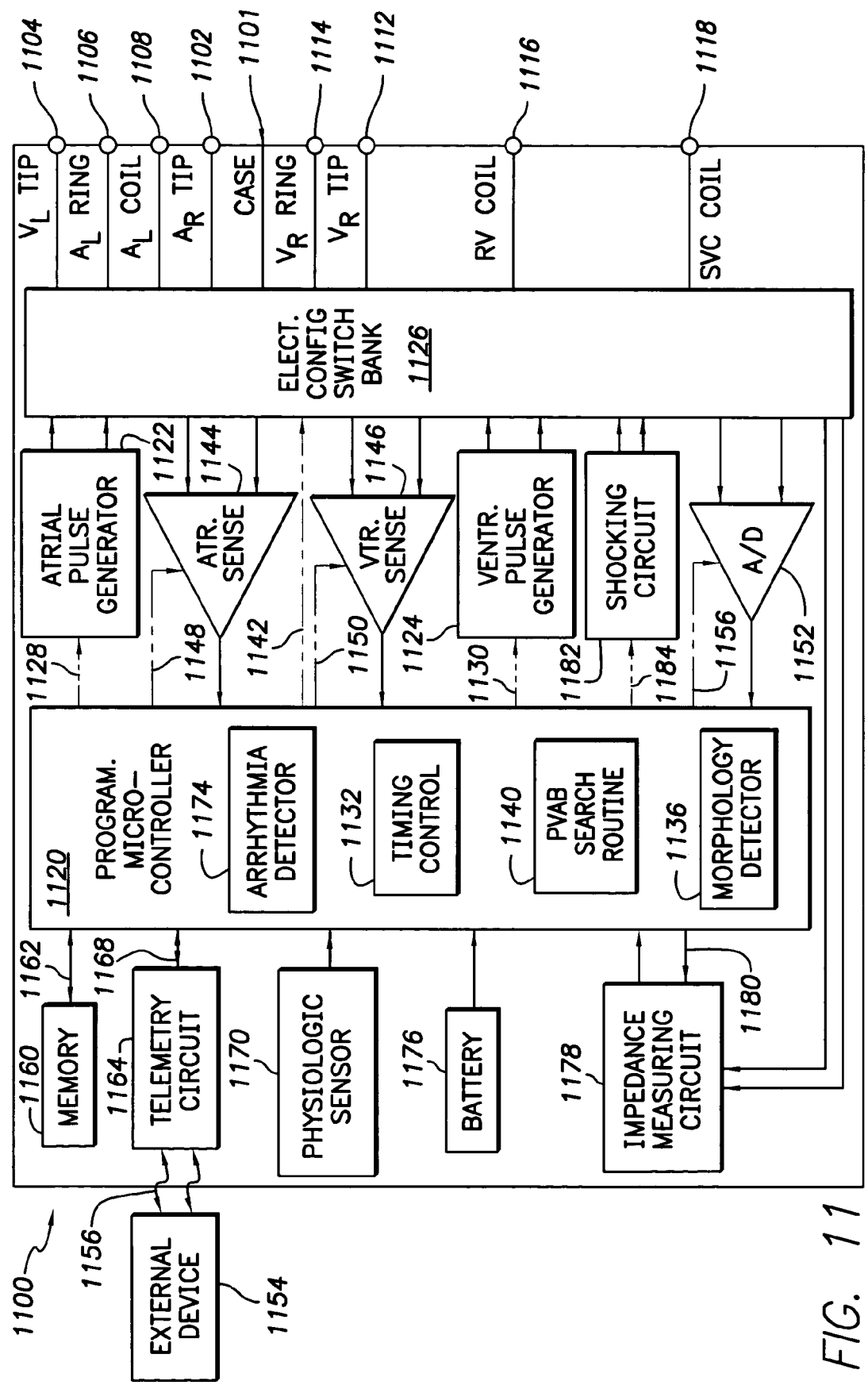
FIG. 11 is a more detailed functional block diagram of a particular embodiment of an implantable cardiac stimulation device.

FIG. 11 is a simplified functional block diagram depicting various components in accordance with another example of a cardiac stimulation device system 1100, as may be incorporated (in whole or part) into an implantable cardiac stimulation device such as, for example, cardiac stimulation device 100 illustrated in FIG. 1. Preferably, the cardiac stimulation device system 1100 is capable of providing pacing stimulation therapies in one or more chambers of the patient's heart for treating various heart conditions such as bradycardia. Additionally, the cardiac stimulation device system 1100 may be configured to provide cardioversion and/or defibrillation therapies to the patient's heart for treating, e.g., fast or slow arrhythmias or other heart conditions. The principles as have been and will be described herein are applicable to pulse generators of varying degrees of sophistication, and are likewise applicable to either single-chamber and multi-chamber devices. It will be understood and appreciated by those skilled in the art that various components or features in the FIG. 11 system 1100 could be duplicated, eliminated, or disabled, in various combinations, while still operating according to the principles as described herein, and that various additional circuits, systems, subsystems, components, or features may be added without departing from the scope and spirit of the basic principles described herein.

As described in greater detail elsewhere herein, the cardiac stimulation device system 1100 preferably is capable of adjusting certain programmed pacing parameters, specifically including certain blanking intervals, according to the specific needs of a patient. An automated or semi-automated search routine preferably facilitates selection of adjustment of one or more post-ventricular atrial blanking (PVAB) intervals. While the cardiac stimulation device system 1100 of FIG. 11 will be generally described in the context of a dual-chamber device with all of pacing, cardioversion, and defibrillation capabilities, it will be understood that the description is also applicable to, e.g., a single-chamber cardiac stimulation device and/or a device that lacks means for delivering cardioversion or defibrillation therapies, or to other alternative embodiments. The depiction in FIG. 11 is thus meant to be illustrative of the features that may be found in a cardiac stimulation device system 1100 but is not intended to limit the scope of the invention in any manner.

As illustrated in FIG. 11, among the electrical connections provided in the cardiac stimulation device system 1100 is a case "electrode" connection 1101 to the housing of the cardiac stimulation device. The case electrode connection 1101 may in some cases be selected, via appropriate programming parameters, to act as the return electrode for various "unipolar" modes. The housing, through the case electrode connection 1101, may further be used as a return electrode for shocking purposes, either alone or in combination with one or more coil electrodes. Further illustrated, from a schematic standpoint, are signal terminals 1102, 1104, 1106, 1108, 1112, 1114, 1116 and 1118 (the names of the electrodes or other component to which the terminals are intended to be attached are shown next to each terminal). Preferably, the housing of the cardiac stimulation device includes a connector (not shown) providing a means for connecting the terminals 1102, 1104, 1106, 1108, 1112, 1114, 1116, and 1118 to their respect electrodes or other components.

For right atrial sensing and pacing, the connector preferably includes a right atrial tip terminal ($A_R$ TIP) 1102 adapted for connection to an atrial tip electrode. For left chamber sensing, pacing, and shocking, the connector preferably includes a left ventricular tip terminal ($V_L$ TIP) 1104, a left atrial ring terminal ($A_L$ RING) 1106, and a left atrial shocking terminal ($A_L$ COIL) 1108, which are adapted for connection to a left ventricular ring electrode, a left atrial tip electrode, and a left atrial coil electrode, respectively.

For right chamber sensing, pacing, and shocking, the connector further preferably includes a right ventricular tip terminal ($V_R$ TIP) 1112, a right ventricular ring terminal ($V_R$ RING) 1114, a right ventricular shocking terminal ($R_V$ COIL) 1116, and an SVC shocking terminal (SVC COIL) 1118, which are adapted for connection to a right ventricular tip electrode, a right ventricular ring electrode, an RV coil electrode, and an SVC coil electrode, respectively.

A programmable microcontroller 1120 is preferably provided in the cardiac device stimulation system 1100 to, among other things, control the various modes of stimulation therapy. As is well known in the art, microcontroller 1120 typically includes a microprocessor, or equivalent control circuitry, designed specifically for controlling the delivery of stimulation therapy, and may further include volatile (e.g., RAM) and/or non-volatile (e.g., ROM) memory, logic and timing circuitry, state machine circuitry, and I/O circuitry. Typically, microcontroller 1120 includes the ability to process or monitor input signals (data) as controlled by a program code stored in a designated block of memory. The specific type of microcontroller 1120 is not critical to the described implementations. Rather, any suitable microcontroller 1120 may be used that is capable of carrying out the functions described herein. The use of microprocessor-based control circuits for performing timing and data analysis functions are well known in the art.

FIG. 11 further shows, in connection with the cardiac device stimulation system 1100, an atrial pulse generator 1122 and a ventricular pulse generator 1124 for generating pacing stimulation pulses to be delivered by the right atrial lead, the coronary sinus lead, and/or the right ventricular lead, preferably via an electrode configuration switch 1126. To provide stimulation therapy in each of the four chambers of the heart, the atrial and ventricular pulse generators 1122, 1124 may include dedicated, independent pulse generators, multiplexed pulse generators, or shared pulse generators. In the example shown in FIG. 11, the pulse generators 1122, 1124 are controlled by the microcontroller 1120 through control signals 1128 and 1130, respectively, which serve the purpose of triggering or inhibiting the stimulation pulses.

The microcontroller 1120 may include, in the form of, e.g., digital circuitry, microcode or program instructions, or a combination thereof, various functional blocks which facilitate control of the various aspects of the cardiac stimulation device system 1100. For example, the microcontroller 1120 may include timing control circuitry 1132 to control the timing of the stimulation pulses (e.g., pacing rate, atrio-ventricular (AV) delay, atrial interconduction (A-A) delay, or ventricular interconduction (V-V) delay, etc.) as well as to keep track of the timing of refractory periods, blanking intervals, noise detection windows, evoked response windows, alert intervals, marker channel timing, etc. These types of timing functions are well known in the art.

Microcontroller 1120 further may include an arrhythmia detector 1174 and a morphology detector 1136. These components can be utilized by the cardiac stimulation device system 1100 to detect and treat various cardiac conditions requiring treatment. The microcontroller 1120 may also include a PVAB search routine module 1190, which may comprise functionality in accordance with embodiments previously described herein for determining and adjusting certain blanking intervals used by the cardiac stimulation device system 1100. The arrhythmia detector 1174, morphology detector 1136, and PVAB search routine module 1190 may be implemented in any suitable manner—e.g., in hardware as part of the microcontroller 1120, or as software/firmware instructions programmed into the device and executed on the microcontroller 1120 during certain modes of operation.

In the example illustrated in FIG. 11, the electronic configuration switch 1126 preferably comprises a plurality of internal switches (not shown) for connecting the desired terminals (e.g., terminals 1102, 1104, 1106, etc.) to the appropriate input/output circuits, thereby providing complete electrode programmability. The electronic configuration switch 1126, in response to a control signal 1142 from the microcontroller 1120, determines the polarity of the stimulation pulses (e.g., unipolar, bipolar, combipolar, etc.) by selectively opening/closing the appropriate combination of internal switches, in a manner well known in the art.

To sense activity in any or all chambers of the heart, atrial sensing circuit 1144 and ventricular sensing circuit 1146 may be selectively coupled to the right atrial lead, coronary sinus lead, and the right ventricular lead, preferably through the electronic configuration switch 1126. The atrial sensing circuit 1144 and ventricular sensing circuit 1146 may include, e.g., dedicated sense amplifiers, multiplexed amplifiers, or shared amplifiers. The electronic configuration switch 1126 preferably determines the "sensing polarity" of the cardiac signal by selectively opening/closing the appropriate internal switches, in a manner well understood in the art. The foregoing features allow the clinician to program the sensing polarity independent of the stimulation polarity.

Each sensing circuit 1144 and 1146 preferably employs one or more low power, precision amplifiers with programmable gain and/or automatic gain control, bandpass filtering, and threshold detection circuitry, as known in the art, to selectively sense the cardiac signal of interest. The automatic gain control assists the cardiac stimulation device system 1100 with sensing the typically low amplitude signal characteristics associated with atrial or ventricular fibrillation.

The outputs of the atrial and ventricular sensing circuits 1144 and 1146 are connected to the microcontroller 1120 which, in turn, is able to trigger or inhibit the atrial and ventricular pulse generators 1122 and 1124, respectively, in a programmable fashion in response to the absence or presence of cardiac activity in the appropriate chambers of the heart. The sensing circuits 1144 and 1146, in turn, receive control signals over signal lines 1148 and 1150 from the microcontroller 1120 for purposes of controlling the gain or threshold of the sensing circuits 1144, 1146, any polarization charge removal circuitry (not shown), and/or the timing of any blocking circuitry (not shown) coupled to the inputs of the sensing circuits 1144, 1146, all in a manner well understood in the art.

For arrhythmia detection, the cardiac stimulation device system 1100 may utilize the atrial and ventricular sensing circuits 1144, 1146 to sense cardiac signals, which can be analyzed to determine whether a particular cardiac rhythm is physiologic or pathologic. The timing intervals between sensed events (e.g., P-waves, R-waves, and T-waves) are preferably classified by the arrhythmia detector 1134 of the microcontroller 1120 by, e.g., comparing the intervals to predefined rate zone limits (e.g., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (such as bradycardia pacing and, if applicable, anti-tachycardia pacing or cardioversion/defibrillation shocks).

Cardiac signals may, in addition to being applied to atrial and ventricular sensing circuits 1144, 1146, also be applied to inputs of an analog-to-digital (A/D) data acquisition system 1152. The A/D data acquisition system 1152 is preferably configured to acquire intracardiac electrogram signals, convert the raw analog data into a digital signal, and store the digital data for later processing and/or telemetric transmission to an external device 1154. The data acquisition system 1152 may be selectively coupled to the right atrial lead, the coronary sinus lead, and the right ventricular lead through the electronic configuration switch 1126 to allow sampling of cardiac signals across any desired pair of electrodes.

Advantageously, the data acquisition system 1152 may be coupled to the microcontroller 1120, or other detection circuitry, for detecting an evoked response from the heart in response to an applied stimulus, thereby aiding in the detection of "capture." Capture occurs when an electrical stimulus applied to the heart is of sufficient energy to depolarize the cardiac tissue, thereby causing the heart muscle to contract. The microcontroller 1120 generally detects a depolarization signal during a window following a stimulation pulse, the presence of which indicates that capture has occurred. The microcontroller 1120 enables capture detection by triggering the ventricular pulse generator 1124 to generate a stimulation pulse, starting a capture detection window using the timing control circuitry 1132 within the microcontroller 1120, and enabling the data acquisition system 1152 via control signal 1156 to sample the cardiac signal that falls in the capture detection window and, based on the amplitude, determines if capture has occurred.

Capture detection may occur on a beat-by-beat basis or on a sampled basis. A capture threshold search can desirably be performed at regular intervals—e.g., once a day during at least the acute phase (e.g., the first 30 days after implantation) and less frequently thereafter. A capture threshold search procedure begins at a desired starting point (e.g., a high energy level, or else the level at which capture is currently occurring) and decreases the energy level until capture is lost. The value at which capture is lost is known as the capture threshold. Thereafter, a safety margin may be added to the capture threshold to arrive at a pacing stimulus energy value.

The microcontroller 1120 is generally coupled, via a data/address bus 1162, to a memory 1160, wherein the programmable operating parameters used by the microcontroller 1120 are stored and modified, as required, in order to customize the operation of the stimulation device system 1100 to suit the needs of a particular patient. Such operating parameters may define, for example, pacing pulse amplitude, pulse duration, electrode polarity, rate, sensitivity, automatic features, arrhythmia detection criteria, and the amplitude, waveshape and vector of each shocking pulse to be delivered to the patient's heart within each respective tier of therapy. The operating parameters may further include, e.g., one or more selectable PVAB intervals (such as a pace PVAB interval and a sense PVAB interval). The memory 1160 is preferably large enough to store a relatively large amount of data (e.g., from the data acquisition system 1152), which may be read out at a later time (by telemetry) and used for subsequent analysis to guide the programming of the device.

Advantageously, the operating parameters of the implantable device system 1100 may be non-invasively programmed into the memory 1160 through a telemetry circuit 1164 in telemetric communication via communication link 1156 with an external device 1154, such as a programmer, transtelephonic transceiver, or a diagnostic system analyzer. The microcontroller 1120 activates the telemetry circuit 1164 with a control signal 1168. The telemetry circuit 1164 may allow intracardiac electrograms (ECGs) and status information relating to the operation of the device system 1100 (as contained in the microcontroller 1120 or memory 1160) to be sent to the external device 1154 through an established communication link 1156.

A post-ventricular atrial blanking (PVAB) interval may be implemented in the cardiac stimulation device system 1100 in a variety of ways. For example, where the ventricular sense amp 1146 provides an interrupt to the microcontroller 1120, the PVAB interval can be implemented by disabling the interrupt from the atrial sense amp 1144 for the duration of the PVAB interval. The PVAB interval may be timed out using, e.g., any general purpose or dedicated timer available to the microcontroller 1120.

The cardiac stimulation device system 1100 can further include one or more physiologic sensors 1170, such as a "rate-responsive" sensor which is used to adjust pacing stimulation rate according to the state of exertion of the patient. The physiological sensor 1170 may alternatively, or in addition, be used to detect changes in cardiac output, changes in the physiological condition of the heart, or diurnal changes in activity (e.g., detecting sleep and wake states). The microcontroller 1120 may be programmed to respond to information received from the physiologic sensor 1170 by, e.g., adjusting the various pacing parameters (such as rate, AV Delay, V-V Delay, etc.) at which the atrial and ventricular pulse generators 1122, 1124, generate stimulation pulses, or by making other dynamic adjustments. While shown in FIG. 11 as being included within the stimulation device, the physiologic sensor 1170 may instead be external to the stimulation device, yet still be implanted within or carried by the patient. Examples of physiologic sensors that may be implemented in cardiac stimulation device system 1100 include sensors that, for example, sense respiration rate and/or minute ventilation, pH of blood, ventricular gradient, and so forth. The physiological sensor 1170 may also be embodied, for example, as a pressure sensor that is coupled to detect RV pressure that is sensed by a ring sensor which can perform dual functions of a ring electrode and a pressure sensor.

The one or more physiological sensors 1170 may further include sensors for detecting position or postural changes. Any sensor capable of sensing such changes, either directly or indirectly, may be used for such a purpose. In particular, the one or more physiological sensors 1170 may include an activity or position sensor (not shown) mounted within the housing of the stimulation device to detect movement in the patient's position. The activity or position sensor may be implemented in many ways, including as a 3D accelerometer, a sensor that detects the earth's magnetic or gravitational fields, a MEMs (micro-electro mechanical) device, and the like. Another sensor that may be used is of the type that detects activity variance. The cardiac stimulation device system 1100 can further include one or more hemodynamic sensors (not shown) for various purposes.

The cardiac stimulation device system 1100 additionally may include a battery 1176 for providing operating power to the circuitry shown in FIG. 11. For an implantable cardiac device employing cardioversion or defibrillation shock therapy, the battery 1176 is preferably capable of operating at low current drains (preferably less than, e.g., 10 μA) for long periods of time, and of providing high-current pulses (for capacitor charging) when the patient requires a shock pulse. The battery 1176 also desirably has a predictable discharge characteristic so that elective replacement time can be detected. As one example, the battery 1176 may be of the lithium/silver vanadium oxide variety.

The cardiac stimulation device system 1100 can further include magnet detection circuitry (not shown), coupled to the microcontroller 1120, to detect when a magnet is placed in near proximity to the cardiac stimulation device. A magnet may be used, for example, by a clinician to perform various test functions of the cardiac stimulation device and/or to signal the microcontroller 1120 that the external programmer 1154 is in place to exchange data with the microcontroller 1120 through the telemetry circuits 1164.

The cardiac stimulation device system 1100 further may include an impedance measuring circuit 1178, enabled by the microcontroller 1120 via a control signal 1180. Examples of uses for an impedance measuring circuit 1178 include, among other things, (1) lead impedance surveillance during the acute and chronic phases for proper lead positioning or dislodgment; (2) electrode operability verification (and automatic switching to an operable pair if dislodgment occurs); (3) measurement of respiration or minute ventilation; (4) measurement of thoracic impedance for determining shock thresholds; (5) detection of whether the device has been implanted; (6) measurement of stroke volume; and (7) detection of the opening of heart valves. The impedance measuring circuit 1178 is advantageously coupled to the electronic configuration switch 1126 so that any desired electrode may be used in connection with the impedance measuring circuit 1178.

In the case where the cardiac stimulation device system 1100 is intended to be a part of an implantable cardioverter/defibrillator (ICD) device, the cardiac stimulation device system 1100, upon detecting the occurrence of an arrhythmia, automatically applies a programmed electrical shock therapy to the heart aimed at terminating the detected arrhythmia. To this end, the microcontroller 1120 controls a shocking circuit 1182 through a control signal 1184 (or set of control signals). The shocking circuit 1182 may be programmed to generate shock pulses of different selectable energy magnitudes—for example, of low (up to 0.5 joules), moderate (0.5-10 joules), or high energy (11 to 40 joules)—as controlled by the microcontroller 1120. Such shock pulses are ordinarily applied to the patient's heart through at least two shocking electrodes, which may generally be selected from the left atrial coil electrode, the RV coil electrode, and/or the SVC coil electrode. The housing of the cardiac stimulation device may act as an active electrode in combination with the RV electrode, or as part of a split electrical vector using the SVC coil electrode, or the left atrial coil electrode (i.e., using the RV electrode as a common electrode).

Cardioversion shocks tend to be of low to moderate energy level (so as to minimize pain felt by the patient), and may be synchronized with an R-wave. Cardioversion therapy tends to be utilized, generally, for the treatment of tachycardia. Defibrillation shocks are generally of moderate to high energy level (e.g., in the range of 5-40 joules), delivered synchronously or asynchronously (since R-waves may be too disorganized during a fibrillation episode). Defibrillation shocks are generally utilized for treating fibrillation. The microcontroller 1120 is preferably capable of controlling the synchronous or asynchronous delivery of the shock pulses, and the provision of synchronous or asynchronous shocks may be either programmable (and may further be tailored to the particular mode or degree of therapy) or may be set by default in whole or part.

While preferred embodiments of the invention have been described herein, many variations are possible which remain within the concept and scope of the invention. Such variations would become clear to one of ordinary skill in the art after inspection of the specification and the drawings. The invention therefore is not to be restricted except within the spirit and scope of any appended claims.

What is claimed is:

1. An implantable cardiac stimulation device, comprising:
    a pulse generator adapted to provide stimulating pulses for application to a patient's heart;
    a detector adapted to detect activity in a ventricle and an atrium of the patient's heart; and
    a controller configured to determine an average atrial rate and an average ventricular rate and to execute a search routine to select a first post-ventricular atrial blanking interval for use after ventricular pace events and a second post-ventricular atrial blanking interval for use after ventricular sense events if a ratio of the average atrial rate and average ventricular rate exceeds a threshold.

2. The implantable cardiac stimulating device of claim 1, wherein at least one of the post-ventricular atrial blanking intervals is programmable.

3. The implantable cardiac stimulating device of claim 1, wherein said controller selects the programmable post-ventricular atrial blanking period interval values from among a plurality of discrete atrial blanking period interval values.

4. The implantable cardiac stimulating device of claim 1, wherein said controller executes said search routine such that the different atrial blanking period interval values are employed in ascending order, and selects for use the atrial blanking period interval value, or a derivative thereof, that first results in failure to detect a far-field R-wave by said detector after expiration of the atrial blanking period interval value.

5. The implantable cardiac stimulating device of claim 1, wherein said controller executes said search routine such that the different atrial blanking period interval values are employed in descending order, and, after detection of a far-field R-wave by said detector after expiration of an applied atrial blanking period interval value, selects for use the last atrial blanking period interval value, or a derivative thereof, that resulted in failure to detect a far-field R-wave by said detector after expiration of the atrial blanking period interval value.

6. The implantable cardiac stimulating device of claim 1, wherein said controller automatically runs said search routine after implantation of said implantable cardiac stimulating device to initially select the programmable post-ventricular atrial blanking period interval values.

7. The implantable cardiac stimulating device of claim 1, wherein said controller is configured to automatically, without manual intervention, run said search routine after implantation of said implantable cardiac stimulating device and after initial selection of the programmable post-ventricular atrial blanking period interval values, to update one or more of the programmable post-ventricular atrial blanking period interval values.

8. The implantable cardiac stimulating device of claim 1, wherein said controller is configured to execute a first search routine to determine a value for said first post-ventricular atrial blanking interval and a second search routine to determine a value for said second post-ventricular atrial blanking interval.

9. The implantable cardiac stimulating device of claim 1, further comprising a non-volatile erasable memory in which the programmable post-ventricular atrial blanking period interval values are stored.

10. A method for use with an implantable cardiac stimulation device, the method comprising:
    detecting activity in an atrium and a ventricle of a patient's heart;
    determining a ratio of an average atrial rate and an average ventricular rate;
    executing a search routine to systematically apply a plurality of different atrial blanking period interval values after corresponding ventricular pace events and corresponding ventricular sense events if the ratio exceeds a threshold;
    after a sensed ventricular event, applying a first post-ventricular atrial blanking period which does not result in detection of far-field R-waves after expiration of the first post-ventricular atrial blanking period; and
    after a paced ventricular event, applying a second post-ventricular atrial blanking period which does not result in detection of far-field R-waves after expiration of the second post-ventricular atrial blanking period wherein the second post-ventricular atrial blanking period is different from the first post-ventricular atrial blanking period.

11. The method of claim 10, wherein selecting the value for at least one of said first post-ventricular atrial blanking period interval and said second post-ventricular atrial blanking period interval comprises selecting values for both said first post-ventricular atrial blanking period interval and said second post-ventricular atrial blanking period interval from among said plurality of available atrial blanking period interval values.

12. The method of claim 11, wherein said plurality of available blanking period interval values comprise discrete values which differ for said first post-ventricular atrial blanking period interval and said second post-ventricular atrial blanking period interval.

13. The method of claim 10, wherein both the first post-ventricular atrial blanking period interval and the second post-ventricular atrial blanking period interval are selected using said search routine.

14. The method of claim 10, wherein said search routine applies said available atrial blanking period interval values in ascending order and selects the discrete atrial blanking period interval value that first results in failure to detect a far-field R-wave after expiration of the discrete atrial blanking period interval value.

15. The method of claim 10, wherein said search routine applies said available atrial blanking period interval values in descending order until a far-field R-wave is detected after expiration of an applied atrial blanking period interval value, and selects the last discrete atrial blanking period interval value that resulted in failure to detect a far-field R-wave after expiration of the atrial blanking period interval value.

16. The method of claim 10, wherein selection of the value for at least one of said first post-ventricular atrial blanking period interval and said second post-ventricular atrial blanking period interval is carried out in response to instructions received from a remote source.

17. A pacing system for providing electrical stimulation to a patient's heart, comprising:
an implantable cardiac stimulation device comprising:
sensing circuitry capable of detecting activity in the atrium and ventricle of a patient's heart;
a pulse generator adapted to provide stimulating pulses for application to at least the atrium of the patient's heart;
memory for durably storing a plurality of post-ventricular atrial blanking interval values, each of said post-ventricular atrial blanking interval values associated with a different type of ventricular event; and
control means configured to determine an average atrial rate and an average ventricular rate and to execute a search routine to systematically apply a plurality of different atrial blanking period interval values after corresponding ventricular pace events and corresponding ventricular sense events if a ratio of the average atrial rate and the average ventricular rate exceeds a threshold and to modify the duration of the atrial blanking period after occurrence of a ventricular event based upon the type of ventricular event by selecting the post-ventricular atrial blanking interval value corresponding to the ventricular event type and which does not result in detection of far-field R-waves after expiration of the selected post-ventricular atrial blanking period.

18. The pacing system of claim 17, wherein said plurality of post-ventricular atrial blanking interval values comprises a first post-ventricular atrial blanking interval value employed after ventricular pace events and a second post-ventricular atrial blanking interval value employed after ventricular sense events.

19. The pacing system of claim 17, wherein said programming means facilitates selection of said at least one selectable post-ventricular atrial blanking interval value from among a plurality of discrete atrial blanking period interval values.

20. The pacing system of claim 17, wherein said control means is further configured to execute a search routine to systematically apply different atrial blanking period interval values and to receive an indication of whether far-field R-waves are detected by said detector after expiration of each applied atrial blanking period interval value.

21. The pacing system of claim 17, wherein said programming means comprises a remote interface whereby selection of at least one of said post-ventricular atrial blanking interval values is carried out in response to instructions received from a remote source.

22. An implantable cardiac stimulation device, comprising:
a pulse generator adapted to provide stimulation pulses for application to a patient's heart;
a detector adapted to detect activity in the ventricle and the atrium of the patient's heart; and
a controller configured to determine an average atrial rate and an average ventricular rate and to execute a search routine to systematically apply a plurality of different atrial blanking period interval values after corresponding ventricular pace events and corresponding ventricular sense events if a ratio of the average atrial rate and the average ventricular rate exceeds a threshold and to provide a first post-ventricular atrial blanking interval after ventricular pace events which does not result in detection of far-field R-waves after expiration of the first post-ventricular atrial blanking period and a second post-ventricular atrial blanking interval after ventricular sense events which does not result in detection of far-field R-waves after expiration of the second post-ventricular atrial blanking period.

23. The implantable cardiac stimulating device of claim 22, wherein both of said first post-ventricular atrial blanking interval and said second post-ventricular atrial blanking interval are programmable.

24. The implantable cardiac stimulating device of claim 23, wherein said controller is configured to execute a first search routine to determine a value for said first post-ventricular atrial blanking interval and a second search routine to determine a value for said second post-ventricular atrial blanking interval.

25. The implantable cardiac stimulating device of claim 24, further comprising a remote interface in communication with said controller, wherein at least one of said first search routine and said second search routine are initiated in response to instructions received from a remote source.

26. The implantable cardiac stimulating device of claim 22, further comprising a remote interface in communication with said controller, for facilitating selection of at least one of said post-ventricular atrial blanking intervals.

* * * * *